United States Patent [19]

Genovesi et al.

[11] Patent Number: 5,445,961

[45] Date of Patent: * Aug. 29, 1995

[54] ISOLATED MICROSCOPE AND ANTHER CULTURE OF MAIZE

[75] Inventors: Anthony D. Genovesi, Sycamore; Richard A. Yingling, DeKalb, both of Ill.

[73] Assignee: DeKalb Genetics Corporation, DeKalb, Ill.

[ * ] Notice: The portion of the term of this patent subsequent to Jun. 21, 2011 has been disclaimed.

[21] Appl. No.: 992,637

[22] Filed: Dec. 18, 1992

Related U.S. Application Data

[63] Continuation-in-part of Ser. No. 543,957, Jun. 26, 1990, abandoned.

[51] Int. Cl.$^6$ .............................................. A01H 4/00
[52] U.S. Cl. ..................... 435/240.5; 800/DIG. 56; 435/240.45; 435/240.48
[58] Field of Search ........... 435/240.4, 240.45, 240.48, 435/240.49, 240.5, 284, 285; 800/200, DIG. 56

[56] References Cited

U.S. PATENT DOCUMENTS 4,672,035   6/1987   Davidonis et al. ................ 435/240.4
7,995,938  12/1992   Genovesi et al. .

FOREIGN PATENT DOCUMENTS

245898A2   4/1987   United Kingdom .

OTHER PUBLICATIONS

Murashige, T., Skoog, F. (1962) A Revised Medium for Rapid Growth and Bioassays with Tobacco Tissue Cultures. Physiol. Plant 15:473–497.

Jensen, C. J. (1974) Chromosome Doubling Techniques in Haploids, in Kasha, K. J. (ed.) Haploids in Higher Plants: Advances and Potentials. Univ. Press, Guelph, pp. 153–190.

Anonymous, 401 Research Group (1975) Primary Study on Induction of Pollen Plants of Zea Mays (English Abstract) Acta. Genetc. Sin. 2:143.

Sunderland, N. (1979) Anther and Pollen Culture 1974–1979, pp. 171 ∝ 183 in The Plant Genome and 2nd Int. Haploid Conference, John Innes Symp.

Miao, S. H. (1980) Effect of Different Ammonium Salts on the Formation of Maize Pollen Embryoids. Acta. Bot. Sin 22:356–359.

Brettell, R. I. S., et al. (1981) Production of Haploid Maize Plants by Anther Culture, Maydica 26:101–111.

Chu, C. C. (1981) The N6 Medium and Its Applications to Anther Culture of Cereal Crops. Proc. Symp. Plant tissue culture, Beijing 1978. Pitman, Boston, pp. 43–50.

Ku, M. K., Cheng, W. C., et al. (1981) Induction Factors and Morphocytological Characteristics of Pollen–Derived Plants in Maize (Zea Mays), Proc. Symp. Plant Tissue Culture, Beijing 1978, Pitman, Boston, pp. 35–42.

Miso, S. H., Kuo, C. S., et al. (1981) Induction of Pollen Plants of Maize and Observations on Their Progeny, Proc. Symp. Plant tissue culture, Beijing 1978. Pitman, Boston, pp. 23–24.

Ting, Y. C., Yu, M., et al. (1981) Improved Anther Culture of Maize (Zea mays). Plant Sci. Lett. 23:139–145.

(List continued on next page.)

*Primary Examiner*—Che S. Chereskin
*Attorney, Agent, or Firm*—Arnold, White & Durkee

[57] ABSTRACT

This invention relates to the regeneration of fertile monocotyledonous plants from a plant composition that contains microspores. A method of the present invention comprises preculturing a plant composition under a plurality of stressful conditions that promote embryogenesis, isolating microspores at a temperature below about 25° C., culturing the microspores in an embryoid/calli induction medium and regenerating a plant from an embryoid/calli. A solid, porous support system for transferring isolated microspores through a series of subcultures containing different media is also provided. The composition of the media are aspects of the invention.

14 Claims, 18 Drawing Sheets

OTHER PUBLICATIONS

Genovesi, A. D. et al., (1982) In Vitro Production of Haploid Plants of Corn via Anther Culture, Crop Sci 22:1137–1144.

Kuo, C. S., et al. (1985) Corn (Zea mays L.): Production of Pure Lines Through Anther Culture, In: Bajaj, YPS (ed.) Biotechnology in Agriculture and Forestry, vol. 2, Crops I, Springer, N.Y. pp. 152–164.

Duncan, D. R., Williams, M. E., et al. (1985) The Production of Callus Capable of Plant Regeneration from Immature Embryos of Numerous Zea Mays Genotypes. Planta 165:322–332.

Pauk, J. (1985) Production of Haploid Plants of Maize (Zea mays L.) Through Androgenesis. Cereal Res. Commun. 13:47–57.

Wei. Z. M. et al. (1986) Callus Formation and Plant Regeneration Through Direct Culture of Isolated Pollen of Hordeum vulgare cv. 'Sabarlis', Theor. Appl. Genet. 72:252–255.

Sorvari, S., (1986) The Effect of Starch Gelantinized Nutrient Media in Barley Anther Cultures, Ann. Agric. Fenn. 25:127–133.

Sorvari, S., (1986) Comparison of Anther Cultures of Barley Cultivars in Barley-Starch and Agar Gelatinized Media, Ann. Agric. Fenn. 25:249–254.

Dieu, P., Becker, M. (1986) Further Studies of Androgenetic Embryo Production and Plant Regeneration from in vitro Cultured Anthers in Maize (Zea mays L.). Maydica 31:245–259.

Petolino, J. F., Jones, A. M., (1986) Anther Culture of Elite Genotypes of Zea mays L. Crop Sci., 26:1027–1074.

Olsen, F. (1987) Induction of Microspore Embryogenesis in Cultured Anthers of Hordeum Vulgare. The Effects of Ammonium Nitrate, Glutamine and Asparagine as Nitrogen Sources, Carlesberg Res. Commun. 52:393–404.

Petolino, J. F., et al. (1987) Genetic Analysis of Anther Culture Response in Maize, Theor. Appl. Genet. 74:284–286.

Keller, W. A., et al. (1987) Haploids from Gametophytic Cells—Recent Developments and Future Prospects, Plant Tiss. and Cell Cul., Alan R. Liss, Inc., pp. 223–241.

Close, K. R., Ludeman, L. A. (1987) The Effect of Auxin-Like Plant Growth Regulators and Osmotic Regulation on Induction of Somatic Embryogenesis from Elite Maize Inbreds. Plant Sci. 52:81–89.

Nitsch, C., Andersen, S., et al. (1987) Production of Haploid Plants of Zea mays and Pennisetum Through Androgenesis. In: Earle E. D., Demarly Y. (eds) Variability in Plants Regeneration from Tissue Culture. Praeger, N.Y., pp. 69–91.

Pace, G. M., Reed, J. N., et al. (1987) Anther Culture of Maize and the Visualization of Embryogenic Microsphores by Fluorescent Microscopy. Theor. Appl. Genet. 73:963–869.

Sletten, M. C., Tomes, D. F., (1987) Plant Recovery from Type I and Type II Embryogenic Callus in Maize. In Vitro 23:26A.

Hunter, et al. (1988) Maltose—The Preferred Carbon Source for Barley Anther Culture, Shell Research Limited.

Barley Anther Culture, Shell Research Limited. Songated, D. D., et al. (1988) Effect of 1 $\alpha$ Aminocyclopropane-1-Carboxylic Acid, Silver Nitrate, and Norbornadiene on Plant Regeneration from Maize Callus Cultures, Plant Cell Rep. 7:262–265.

Songated, D. D., et al. (1988) Effect of 1-Aminocyclopropane-1-Carboxylic Acid, Silver Nitrate, and Norbornadiene on Plant Regeneration from Maize Callus Cultures, Plant Cell Rep. 7:262–265.

Petolino, J. F., et al. (1988) Selection for Increased Anther Culture Response in Maize, Theor. Appl. Genet. 76:157–159.

Rhodes, C. A., Lowe, K. S., Ruby, K. L. (1988) Plant Regeneration from Protoplasts Isolated from Embryogenic Maize Cell Cultures. Biotechnology 6:56–60.

Wan, Y., et al. (1989) Efficient Production of Doubled Haploid Plants Through Colchicine Treatment of Anther-Derived Maize Cells, Theor. Appl. Genet. 7:889–892.

Pescitelli, S. M., et al. (1989) High Frequency Androgenesis from Isolated Microsphores of Maize, Plant Cell Rep. 7:673–676.

Coumans, M. P., et al. (1989) Plant Development from Isolated Microspores of Zea mays L., Plant Cell Rep. 7:618–621.

Vain, P., et al. (1989) Enhancement of Production and Regeneration of Embryogenic Type II Callus in Zea mays L. by AqNO3, Plant Cell. Tissue and Organ Culture 18:143–151.

(List continued on next page.)

OTHER PUBLICATIONS

Personal Communication, Finn Dok to Dennis Genovesi (1989).
Personal Communication, Finn Dok to Dennis Genovesi (1989).
Personal Communication, Finn Dok to Dennis Genovesi (1989).
Genovesi, A. D. (1990) Maize (Zea mays L.): In Vitro Production of Haploids Biotech. in Agric. and Forestry, vol. 12, Haploids in Crop Improvement I (ed. by YPS. Bajaj), pp. 176–203.
Pescitelli, S. M., et al. (1990) Isolated Microspore Culture of Sucrose Level, Plant Cell Rep. 8:628–631.
Sigma ad, Membrane Rafts, (1990).
Roberts–Oehlschlager, S. L., Dunwell, J. M., Faulks, R. (1990). Changes in the Sugar Content of Barley Anters During Culture on Different Carbohydrates. Plant Cell. Tissue and Organ Culture 22:77–85.
Pescitelli, et al. (1989) Plant Cell Reports 7: 673–676.
Pace, et al. (1987) Theor. Appl. Genet. 73: 863–869.
Wei, et al. (1986) Theor. Appl. Genet. 72: 252–255.
Roberts–Oehlschlager et al. (1990) Plant Cell, Tissue, and Organ Culture 22: 77–85.
Wan, et al. (1989) Theor Appl. Genet. 7: 889–892.
Dok (Communicaton of Jul. 15, 1989) Fin Dok to Dennis Genovesi.
Genovesi, et al. (Nov.–Dec. 1982) Crop Science 22: 1137–1144.
Sharp et al., in Crop Breeding a contemporary basis (Vose, et al., eds.) Pergamon Press, Oxford, 1984, pp. 358–360.
Sigma Catalog (Spring 1990).
Cheng, et al. (16 May 1977) Science 198: 306–307.
Sorvari (1986) Annales Agriculturae Fenniae 25: 127–133, Seria Agriculturea No. 76.
Sharp, et al. (1972) Planta (Berl.) 104: 357–361.

ISOLATED MICROSCOPE AND ANTHER CULTURE OF MAIZE

CROSS-REFERENCE TO RELATED APPLICATION

This application is a continuation-in-part of U.S. patent application Ser. No. 07/543,957, filed on Jun. 26, 1990, now abandoned, the disclosure of which is incorporated herein by reference.

BACKGROUND OF THE INVENTION

1. Field of the Invention

This invention relates to methods for the production of monocotyledonous plants from microspore cultures and from anther cultures. These methods are especially suitable for maize. In other aspects, this invention relates to the regenerated plants, and to seeds and progeny of the regenerated plants derived from cultured anthers or microspores.

2. Description of the Related Art

Ever since the human species emerged from the hunting-gathering phase of its existence, and entered an agricultural phase, a major goal of human ingenuity and invention has been to improve crop yield and to alter and improve the characteristics of plants. In particular, man has sought to alter the characteristics of plants to make them more tasty and/or nutritious, to produce increased crop yield or to render plants more adaptable to specific environments. Recently, plant products which have uses other than as food are becoming increasingly commercially attractive.

Up until recent times, crop and plant improvements depended on selective breeding of plants with desirable characteristics. Initial breeding success was probably accidental, resulting from observation of a plant with desirable characteristics, and use of that plant to propagate the next generation. However, because such plants had within them heterogenous genetic complements, it was unlikely that progeny identical to the parent(s) with the desirable traits would emerge. Nonetheless, advances in controlled breeding have resulted from both increasing knowledge of the mechanisms operative in hereditary transmission, and by empirical observations of results of making various parental plant crosses.

Crop and plant improvement is a major area of commercial interest, for example, monocots L. (corn, maize) is a major worldwide cereal crop. In the continental United States alone, an estimated 70–82 million acres of corn is planted yearly. Unfortunately, current methods for improving inbred corn lines are time consuming, labor intensive, and risky. Seed from those plants shown to retain the desired new characteristics are selected for further breeding. Only after a period of several years can a sufficient seed stock of the inbred corn displaying the desired characteristic be accumulated for commercial breeding purposes. Inbred lines must then typically be crossed to produce hybrids, because inbred lines generally have lower production characteristics, e.g., amount of grain (kernels) per ear, than do hybrids. The process of developing inbred parents generally takes from 4–6 years. Another 3–4 years is required for field testing for a total of 7–10 years.

By use of anther and pollen (microspore) cultures, the time periods to introduce improvements into crops, may be reduced from 4–6 years, to about 1–2 years. Chinese scientists have pioneered this area (Anon., 401 Research Group, 1975). Anthers are the structures that contain the male gametophytes, the haploid microspores or pollen. Microspores have a single nucleus whereas mature pollen have 3 nuclei. These in vitro methods make it possible to test a larger number of new mutations and gene combinations and to select among these for desirable traits. More extensive and imaginative genetic manipulations are also facilitated, such as production of transgenic plants.

Various general methods, including anther and isolated microspore cultures, have been used in a large number of crops, e.g. tobacco and barley, to produce organisms with haploid genetic complements. "Haploids" contain only one-half of the chromosome number present in somatic cells. Somatic cells are those other than gametic cells, the latter being inherently haploid. Haploid complements may also be doubled to produce homozygous diploids. The production of doubled haploid plants is one way to produce homozygous lines. (see review in Kuo, et al. 1985). Haploid plants have both male and female sex organs and produce ears with good seed through self-pollination when chromosomes are doubled. Their seeds may also be used to make F1 crosses to test field performance as hybrids.

As mentioned above, pollen grains develop from microspores which are in turn produced by meiosis in pollen mother cells. The plants resulting from pollen cultures are also usually haploid and may be sterile. To remedy this, the chromosome complement may be doubled by various agents, e.g. colchicine, a mitotic spindle inhibitor, the use of which results in chromosome duplication without cell division. (Jensen, 1974). Occasionally, chromosome doubling occurs spontaneously. The plants resulting from induced or spontaneous chromosome doubling are diploid. Doubling of haploid complements allows homozygous lines to be produced from heterozygous parents in a single generation. Another advantage of this process is that resulting plants breed true, making the selection process for desirable traits more efficient. Microspore culture followed by chromosome doubling is one method of producing doubled haploids.

Factors that affect the frequency of in vitro plant production include genotype, donor plant physiology, the stage of pollen development, pretreatment conditions and the concentrations and nature of ingredients in the media used for culture and regeneration (see review in Keller, et al., 1987). For example, sucrose levels, hormones and additives to culture media affect success. To illustrate the effect of media factors, the effect of one media (N6) supplemented with 2,4-dichlorophenoxyacetic acid (2,4-D), kinetin and other ingredients, is presented by Kuo, supra in his Table 4.

Since the first report by the Chinese of the successful anther culture of maize using an agar solidified medium, improvements have resulted from altering culture conditions, but optimum culture requirements leading to production of plants for commercial use have been elusive. Attempts have been made to adjust media, pretreatment temperature, incubation temperature, and genotype. (Petolino and Jones, 1986). Sorvari et al. (1986) have compared agar-based with starch-based media solidifiers and placed polyester nets on the media to prevent anthers from sinking in. That the response to anther culture is genetically determined was illustrated by the increased response to anther culture of the $F_1$ progeny plants derived from anther culture, compared to response of the parental lines used for culture. (Petolino et al., 1988).

Instead of culturing entire anthers, isolated microspores may be cultured. Recently, there have been reports of culturing maize isolated microspores (Coumans, et al., 1989; Pescitelli, et al., 1989).

The use of mannitol and of cold temperature pretreatment have been explored separately as a means for increasing the frequency of embryoid formation from isolated microspores. (Wei et al., 1986). Wei et al. applied mannitol pretreatment to isolated barley pollen, but had limited success, possibly because the methods were applied to binucleate pollen, whereas uninucleate pollen (microspores) are believed to be the most responsive in culture. Uninucleate cells most likely lost viability during isolation from the anthers. If mannitol pretreatment was applied to whole anthers containing microspores then results were said to be better.

The ultimate goal of anther and microspore culture is to produce plants. Plant regeneration from in vitro cultures of maize initially used organized tissues for the culture. Plant regeneration from single somatic cells of maize following protoplast isolation was reported by Rhodes et al. (1988), but no seed was recovered. Plant regeneration from isolated microspores has been reported for various cereal species, including corn, (Coumans, et al., 1989; Pescitelli et al., 1989) barley, rice and wheat.

Coumans, et al. pretreated tassels for 14 days at 8° C., and recovered isolated microspores by homogenization of tassel fragments by use of a refrigerated blender. The percentage of microspore-derived plants was low, less than 0.1% of the plated microspores. However, a few plants with viable pollen were produced.

In summary, although some progress has been made in producing plants from anther or isolated microspore culture, "attempts at utilizing haploids in maize breeding have been frustrated by the lack of a reliable means of generating sufficient numbers of doubled haploid lines from a broad spectrum of commercially-useful germplasm." (Petolino et al., 1988). There is a need for improved methods for culturing haploid cells and regenerating fertile plants from the cultured haploids. These methods need to be successful in commercially desirable crop lines.

The inventors have developed new and improved culture techniques for general use in regenerating fertile plants from haploid anther or isolated microspore cultures. They have demonstrated that these methods are successful for commercially desirable lines, for example, those characterized by high production characteristics in maize. The inventors have addressed the major problems in culture of haploids, that is, low initial response frequency as determined by embryo-like growth, difficulties in plant regeneration, and difficulties in chromosome doubling to make diploids from haploids, the latter process leading to fertile plants. The inventors have combined environmental stress conditions which divert the microspores from microsporogenesis to embryogenesis, for example, by combination of stress factors comprising medium components such as mannitol, and cold pretreatments, to recover surprisingly high yields of calli/embryoids and of regenerated fertile plants.

SUMMARY OF THE INVENTION

This invention relates generally to methods for the production of monocotyledonous plants, and in particular fertile plants, from anther cultures or from isolated microspore cultures. Monocotyledonous plants include plants such as maize and barley. Many of these have important commercial value as crops. Methods to shorten the time required for improvement of crops by integrating new genetic traits are disclosed in this invention. The methods of regenerating plants from anther or microspore cultures also facilitate genetic manipulations directed at plant improvement. For example, nucleic acid segments may be introduced into microspores for integration into the chromosomes and expression at the whole plant level. This provides a method for transformation of plants to produce transgenic plants by incorporating large segments of DNA, even artificial chromosomes.

In more general aspects, the invention presents a new methodology for the production of monocotyledonous plants which comprises subjecting plant compositions containing microspores to a combination of stresses. The protocol consists of pretreating a plant composition, for example, organs such as tassels and anthers containing microspores, under conditions which divert the microspores from gametophytic development to that of embryogenic development. The pretreatment includes incubation of the plant composition if it includes tassels, at a cold temperature which is a stress factor. As an additional stress factor in the environment, anthers are dissected into a preculture medium, an embodiment comprising a sugar alcohol such as mannitol. Mannitol may be capable of inducing starvation as the stress factor. Microspores are then isolated from the anther wall in an isolation medium capable of maintaining microspore viability and embryogenic potential. These isolated microspores are then exposed to an embryoid/callus promoting medium. The induced embryoid/callus structures may then be subcultured into a series of media which are capable of inducing tissue development, for example, roots and shoots. These medium may be designated maturation and regeneration medium. If desired, intact plants may then be regenerated in regeneration media. A portion of these plants are capable of producing seeds and progeny. These seeds and progeny are also within the scope of this invention.

A preferred method for producing fertile monocotyledonous plants from microspore cultures will generally include the following steps:

A plant composition, for example, organs such as tassels or anthers, is obtained which includes the microspores which will be cultured to produce regenerated plants. For example, if the plant organ is a tassel, tassels may be removed from the plants and incubated at a cold temperature. Tassels contain the anthers which in turn enclose the microspores. Microspores develop into pollen.

For plant breeding applications, elite germplasm is preferred. Furthermore, anther culture/microspore culture with permissive genotypes from an elite pedigree are most preferred. Elite is defined in a commercial context as the most high yielding lines. A permissive genotype is one capable of producing embryoids and in turn regenerated plants after anther or microspore culture. In the case of corn, the most permissive genotypes are those $F_1$ hybrids resulting from crosses of inbreds derived from the public germplasm "Stiff Stalk Synthetic."

For anther/microspore culture, if tassels are the plant composition, they are preferably selected at a stage when the microspores are uninucleate, that is, include only one, rather than 2 or 3 nuclei. Methods to determine the correct stage are well known to those skilled in the art and include mitramycin fluorescent staining (Pace et al., 1987), trypan blue (preferred) and acetocarmine squashing. The mid-uninucleate microspore stage has been found to be the developmental stage most responsive to the subsequent methods disclosed to ultimately produce plants.

Although the microspore-containing plant organs such as tassels may generally be pretreated at any cold temperature below about 25° C., a range of 4°–25° C. is preferred, and a range of 8°–14° is particularly preferred. If one chooses to use corn tassels, a preferred temperature is about 10° C. Although other temperatures may yield embryoids and regenerated plants, these cold temperatures produce optimum response rates compared to pretreatment at temperatures outside the preferred range. Response rate is measured as either the number of embryoids or the number of regenerated plants per number of microspores initiated in culture.

Although not required, when tassels are employed as the plant organ, it is generally preferred to sterilize their surface. Following surface sterilization of the tassels, for example, with a solution of calcium hypochloride, the anthers are removed from about 70–150 spikelets (small portions of the tassels) and placed in a preculture or pretreatment medium. Larger or smaller amounts may be used depending on the number of anthers.

When one elects to employ tassels directly, the tassels are preferably pretreated at a cold temperature for a predefined time, preferably at 10° C. for about 4 days for maize. However, other times for pretreatment are within the scope of this invention, as long as isolated microspores will result in regenerated plants, e.g. 1 day at 10° C., to 14 days at 10° C. After the pretreatment of the whole tassel at the cold temperature, dissected anthers are further pretreated in an environment that is capable of diverting microspores from their developmental pathway. About 300 anthers are generally floated in 3 ml of medium contained in a 60 mm dish, for example a petri dish, or in any other laboratory dish of approximately the same size. The function of the preculture medium is to switch the developmental program from one of pollen development to that of embryoid/callus development.

In one embodiment, a preculture medium can function to favor the development of tissue that has been transformed with an exogenous DNA molecule. In accordance with such an embodiment, a preculture medium can comprise a growth regulator such as dicamba.

An embodiment of such an environment in the form of a preculture medium includes a sugar alcohol, for example mannitol or sorbitol, inositol or the like. The combination of stresses comprising predefined temperatures and an embryogenic-promoting environment is an important aspect of this invention. An exemplary synergistic combination is the use of mannitol at a temperature of about 10° C. for a period ranging from about 10–14 days. In a preferred embodiment, 3 ml of 0.3 M mannitol combined with 50 mg/l of ascorbic acid, silver nitrate and colchicine is used for incubation of anthers at 10° C. for between 10 and 14 days. Another embodiment is to substitute sorbitol for mannitol. The colchicine produces chromosome doubling at this early stage. The chromosome doubling agent is preferably only present at the preculture stage.

It is believed that the mannitol or other similar carbon structure or environmental stress induces starvation and functions to force the microspores to focus their energies on entering developmental stages. The cells are unable to use, for example, mannitol as a carbon source at this stage. It is believed that these treatments confuse the cells causing them to develop as embryoids and plants from microspores. Dramatic increases in development from these haploid cells, as high as 25 embryoids in $10^4$ microspores, have resulted from using these methods.

In those embodiments where microspores are obtained from anthers, microspores may be released from the anthers into an isolation medium following the mannitol preculture step. One method of release is by disruption of the anthers, for example, by chopping the anthers into pieces with a sharp instrument, such as a razor blade, scalpel or waring blender. The resulting mixture of released microspores, anther fragments and isolation medium are then passed through a filter in order to separate the microspores from the anther wall fragments. An embodiment of a filter is a mesh, more specifically, a nylon mesh of about 112 μm pore size. The filtrate which results from filtering the microspore-containing solution is preferably relatively free of anther fragments, cell walls and other debris.

In a preferred embodiment, isolation of microspores is accomplished at a temperature below about 25° C. and, preferably at a temperature of less than about 15° C. Preferably, the isolation media, dispersing tool (e.g., razor blade) funnels, centrifuge tubes and dispersing container (e.g., petri dish) are all maintained at the reduced temperature during isolation. The use of a precooled dispersing tool to isolate maize microspores has been reported (Gaillard, et al., 1991).

Where appropriate and desired, the anther filtrate is then washed several times in isolation medium. For best results, washing and subsequent centrifugation is repeated approximately three times. The purpose of the washing and centrifugation is to eliminate any toxic compounds which may be contained in the non-microspore part of the filtrate which are created by the chopping process. The centrifugation is usually done at decreasing spin speeds, for example, 1000, 750, and finally 500 rpms.

The result of the foregoing steps is the preparation of a relatively pure suspension of microspores. Pure refers to the fact that the microspores are relatively free of debris and anther remnants. Isolated microspores refers to individual microspores separated from containment in the anther wall during culture to embryoids/calli.

To isolate microspores, an isolation media is preferred. An isolation media is capable of separating the microspores from the anther walls while maintaining their viability and embryogenic potential. An illustrative embodiment of the isolation media into which microspores are released from the disrupted anthers includes a 6% sucrose or maltose solution combined with an antioxidant such as 50 mg/l of ascorbic acid, 0.1 mg/l biotin and 400 mg/l of proline, combined with 10 mg/l of nicotinic acid and 0.5 mg/l $AgNO_3$. In another embodiment, the biotin and proline are omitted.

An isolation media preferably has a higher antioxidant level where used to isolate microspores from a donor plant (a plant from which a plant composition containing a microspore is obtained) that is field grown in contrast to greenhouse grown. A preferred level of ascorbic acid in an isolation medium is from about 50 mg/l to about 125 mg/l and, more preferably from about 50 mg/l to about 100 mg/l.

One may find particular benefit in employing a support for the microspores during culturing and subculturing. Virtually any support which maintains the cells near the surface of the media will provide some benefits. The microspore suspension is layered onto a support, for example by pipetting. There are several types of supports which are suitable and are within the scope of the invention. An illustrative embodiment of a solid support is a Transwell ® culture dish. Another embodiment of a solid support for development of the microspores is a bilayer plate wherein liquid media is on top of a solid base. Other embodiments include a mesh or a millipore filter. Preferably, the solid support is a nylon mesh in the shape of a raft. A raft is defined as an approximately circular support material which is capable of floating slightly above the bottom of a tissue culture vessel, for example, a petri dish, of about a 60 or 100 mm size, although any other laboratory tissue culture vessel will suffice. In an illustrative embodiment, the raft is about 55 mm in diameter.

Culturing isolated microspores on a solid support, for example, on a 10 $\mu$m pore nylon raft floating on 2.2 ml of medium in a 60 mm petri dish, prevents microspores from sinking into the liquid medium and thus avoiding low oxygen tension. These types of cell supports enable the serial transfer of the nylon raft with its associated microspore/embryoids ultimately to full strength medium containing activated charcoal and solidified with, for example, Gelrite. The charcoal is believed to absorb toxic wastes and intermediaries. The solid medium allows embryoids to mature.

The liquid medium passes through the mesh while the microspores are retained and supported at the medium-air interface. The surface tension of the liquid medium in the petri dish causes the raft to float. The liquid is able to pass through the mesh, consequently, the microspores stay on top. The mesh remains on top of the total volume of liquid medium. An advantage of the raft is to permit diffusion of nutrients to the microspores. Use of a raft also permits transfer of the microspores from dish to dish during subsequent subculture with minimal loss, disruption or disturbance of the induced embryoids that are developing. The rafts represent an advantage over the multi-welled Transwell ® plates, which are commercially available from Costar, in that the commercial plates are expensive. Another disadvantage of these plates is that to achieve the serial transfer of microspores to subsequent media, the membrane support with cells must be peeled off the insert in the wells. This procedure does not produce as good a yield nor as efficient transfers, as when a mesh is used as a vehicle for cell transfer.

If pipetting is chosen to place the microspore suspension onto a solid support, for example, onto a nylon mesh raft, an illustrative embodiment is to pipet about $7-8 \times 10^4$ microspores per dish, wherein a dish is defined as a 60 mm petri dish with 2.2 ml of medium.

The culture vessels may be further defined as either (1) a bilayer 60 mm petri plate wherein the bottom 2 ml of medium are solidified with 0.7% agarose overlayed with 1 mm of liquid containing the microspores; (2) a nylon mesh raft wherein a wafer of nylon is floated on 1.2 ml of medium and 1 ml of isolated microspores is pipetted on top; or (3) Transwell ® plates wherein isolated microspores are pipetted onto membrane inserts which support the microspores at the surface of 2 ml of medium.

After the microspores have been isolated, they are cultured in a low strength anther culture medium until about the 50 cell stage when they are subcultured onto an embryoid/callus maturation medium. Medium is defined at this stage as any combination of nutrients that permit the microspores to develop into embryoids or callus. Many examples of suitable embryoid/callus promoting media are well known to those skilled in the art. These media will typically comprise mineral salts, a carbon source, vitamins, growth regulations. A solidifying agent is optional. A preferred embodiment of such a media is referred to by the inventor as the "D medium" which typically includes 6N1 salts, AgNO$_3$ and sucrose or maltose.

In an illustrative embodiment, 1 ml of isolated microspores are pipetted onto a 10 $\mu$m nylon raft and the raft is floated on 1.2 ml of medium "D" containing sucrose or, preferably maltose. Both calli and embryoids may develop. Calli are undifferentiated aggregates of cells. Type I is a relatively compact, organized and slow growing callus. Type II is a soft, friable and fast-growing one. Embryoids are aggregates exhibiting some embryo-like structures. The embryoids are preferred for subsequent steps to regenerating plants. Culture medium "D" is an embodiment of medium that follows the isolation medium and replaces it. Medium "D" promotes growth to an embryoid/callus. This medium comprises 6N1 salts at ½ the strength of a basic stock solution, (major components) and minor components, plus 12% sucrose or, preferably 12% maltose, 0.1 mg/l B1, 0.5 mg/l nicotinic acid, 400 mg/l proline and 0.5 mg/l silver nitrate. Silver nitrate is believed to act as an inhibitor to the action of ethylene. Multi-cellular structures of approximately 50 cells each generally arise during a period of 12 days to 3 weeks. Serial transfer after a two week incubation period is preferred.

After the petri dish has been incubated for an appropriate period of time, preferably two weeks, in the dark at a predefined temperature, the raft bearing the dividing microspores is transferred serially to solid based media which promotes embryo maturation. In an illustrative embodiment, the incubation temperature is 30° C. and the mesh raft supporting the embryoids is transferred to a 100 mm petri dish containing the 6N1-TGR-4P medium, an "anther culture medium." This medium contains 6N1 salts, supplemented with 0.1 mg/l TIBA, 12% sugar (sucrose, maltose or a combination thereof), 0.5% activated charcoal, 400 mg/l proline, 0.5 mg/l B, 0.5 mg/l nicotinic acid, and 0.2% Gelrite and is capable of promoting the maturation of the embryoids. Higher quality embryoids, that is, embryoids which exhibit more organized development, such as better shoot meristem formation without precocious germination were typically obtained with the transfer to full strength medium compared to those resulting from continuous culture using only, for example, the isolated microspore culture (IMC) Medium "D." The maturation process permits the pollen embryoids to develop further in route toward the eventual regeneration of plants. Serial transfer occurs to full strength solidified 6N1 medium using either the nylon raft, the Transwell ® membrane or bilayer plates, each one requiring the movement of developing embryoids to permit further development into physiologically more mature structures.

In an especially preferred embodiment, microspores are isolated in an isolation media comprising about 6% maltose, cultured for about two weeks in an embryoid/calli induction medium comprising about 12% maltose and then transferred to a solid medium comprising about 12% sucrose.

At the point of transfer of the raft after about two weeks incubation, embryoids exist on a nylon support. The purpose of transferring the raft with the embryoids to a solidified medium after the incubation is to facilitate embryo maturation. Mature embryoids at this point are selected by visual inspection indicated by zygotic embryo-like dimensions and structures and are transferred to the shoot initiation medium. It is preferred that shoots develop before roots, or that shoots and roots develop concurrently. If roots develop before shoots, plant regeneration may be impaired. To produce solidified media, the bottom of a petri dish of approximately 100 mm is covered with about 30 ml of 0.2% Gelrite solidified medium. A sequence of regeneration media are used for whole plant formation from the embryoids.

During the regeneration process, individual embryoids are induced to form plantlets. The number of different media in the sequence may vary depending on the specific protocol used. Finally, a rooting medium is used as a prelude to transplanting to soil. When plantlets reach a height of about 5 cm, they are then transferred to pots for further growth into flowering plants in a greenhouse by methods well known to those skilled in the art.

Plants have been produced from isolated microspore cultures by the methods disclosed herein, including self-pollinated plants. The rate of embryoid induction was much higher with the synergistic preculture treatment consisting of a combination of stress factors, including a carbon source which may be capable of inducing starvation, a cold temperature and colchicine, than has previously been reported. An illustrative embodiment of the synergistic combination of treatments leading to the dramatically improved response rate compared to prior methods, is a temperature of about 10° C., mannitol as a carbon source, and 0.05% colchicine. It had not been expected that the response rate from combining these stresses, each of which has resulted in regenerating plants from anther and microspore cultures, would exceed that expected from only additive effects of the results of pretreatment with each of these factors separately.

Results so far indicate that the response is at least about 25 calli/embryoids per $10^4$ microspores cultured. About 1 out of every 6 responses gives rise to totipotent cultures, that is, cultures that are able to regenerate entire plants. Regenerated plants produced in this manner are sexually fertile about 25% of the time. These results are better than those previously reported from isolated microspore culture using any of the separate pretreatments disclosed in this invention, rather than the combination of pretreatment factors which is an aspect of this invention.

Some additional comments are in order regarding the media used in the various culture and regeneration steps. The inclusion of ascorbic acid, an anti-oxidant, in the isolation medium is preferred for maintaining good microspore viability. However, there seems to be no advantage to including mineral salts in the isolation medium. The osmotic potential of the isolation medium was maintained optimumly with about 6% sucrose, although a range of 2% to 12% is within the scope of this invention.

In an embodiment of the embryoid/callus organizing media, mineral salts concentration in IMC Culture Media "D" is ($\frac{1}{8}\times$), the concentration which is used also in anther culture medium. The 6N1 salts major components have been modified to remove ammonium nitrogen. Osmotic potential in the culture medium is maintained with about 12% sucrose and about 400 mg/l proline. Silver nitrate (0.5 mg/l) was included in the medium to modify ethylene activity. The preculture media is further characterized by having a pH of about 5.7–6.0. Silver nitrate and vitamins do not appear to be crucial to this medium but do improve the efficiency of the response.

This invention is also directed to methods for the production of monocotyledonous plants from a plant culture system consisting of whole anther cultures. An example of a monocotyledonous plant for which these methods are appropriate is maize.

There are some basic similarities of anther culture methods and microspore culture methods with regard to the media used. A difference from isolated microspore cultures is that undisrupted anthers are cultured, so that support, e.g. a nylon mesh support, is not needed. The first step in developing the anther cultures is to incubate tassels at a cold temperature. A cold temperature is defined as less than 25° C. More specifically, the incubation of the tassels is preferably performed at about 10° C. A range of 8°–14° C. is also within the scope of the invention. The anthers are then dissected from the tassels, preferably after surface sterilization using forceps, and placed on solidified medium. An example of such a medium is designated by the inventors as 6N1-TGR-P4.

The anthers are then treated with environmental conditions that are combinations of stresses that are capable of diverting microspores from gametogenesis to embryogenesis. It is believed that the stress effect of sugar alcohols in the preculture medium, for example, mannitol, is produced by inducing starvation at the predefined temperature. In one embodiment, the incubation pretreatment is for about 14 days at 10° C. It was found that treating the anthers in addition with a carbon structure, an illustrative embodiment being a sugar alcohol, preferably, mannitol, produces dramatically higher anther culture response rates as measured by the number of eventually regenerated plants, than by treatment with either cold treatment or mannitol alone. These results are particularly surprising in light of teachings that cold is better than mannitol for these purposes, and that warmer temperatures interact with mannitol better.

To incubate the anthers, they are floated on a preculture medium which diverts the microspores from gametogenesis, preferably on a mannitol carbon structure, more specifically, 0.3 M of mannitol plus 50 mg/l of ascorbic acid. 3 ml is about the total amount in a dish, for example, a tissue culture dish, more specifically, a 60 mm petri dish. Anthers are isolated from about 120 spikelets for one dish yields about 360 anthers.

Another aspect of the invention is the use of chromosome doubling agents in the preculture media for anther cultures. Several techniques for doubling chromosome number (Jensen 1974; Wan, et al. 1989) have been described. Colchicine is one of the doubling agents. However, developmental abnormalities arising from in vitro cloning are further enhanced by colchicine treatments, and previous reports indicated that colchicine is toxic to microspores. The inventors have added colchicine in increasing concentrations during mannitol pretreatment prior to anther culture and microspore culture and achieved improved percentages.

An illustrative embodiment of the combination of a chromosome doubling agent and preculture medium is one which contains colchicine. In a specific embodiment, the colchicine level is preferably about 0.05%. The anthers remain in the mannitol preculture medium with the additives for about 10 days at 10° C. Anthers are then placed on maturation media, for example, that designated 6N1-TGR-P4, for 3 to 6 weeks to induce embryoids. If the plants are to be regenerated from the embryoids, shoot regeneration medium is employed, as in the isolated microspore procedure described in the previous sections. Other regeneration media may be used sequentially to complete regeneration of whole plants.

The anthers are then exposed to embryoid/callus promoting medium, for example, that designated 6N1-TGR-P4 in order to obtain callus or embryoids. The embryoids are recognized by identification visually of embryonic-like structures. At this stage, the embryoids are transferred serially to a series of regeneration media. In an illustrative embodiment, the shoot initiation medium comprises BAP (6-benzyl-amino-purine) and NAA (naphthalene acetic acid). Regeneration protocols for isolated microspore cultures and anther cultures are similar.

This invention also relates to plants, seeds and progeny derived from either microspore or anther cultures by the methods of microspore culturing or anther culturing disclosed herein. Also within the scope of the invention are seeds and progeny derived from said plants. Haploid and diploid plants are produced. The seed may be derived by well-established techniques of harvesting from mature plants or by replanting the harvested seed and obtaining seed from descendant plants. The plants may also be produced by self-fertilization or by chromosome doubling after microspore or anther culture.

An advantage of this invention is to achieve plant regeneration incorporating new and desirable traits, and to produce inbred lines, in about one year instead of five to six years required by classical breeding. These methods will be useful in transformation of DNA segments into pollen. Transfer of large segments of DNA may be facilitated by transfer into pollen rather than directly into cells of, for example, embryogenic callus. Examples of the large DNA segments to transfer comprise artificial chromosomes or other large intact gene sequences.

Anther and isolated microspore culture should be viewed as an additional approach to classical plant breeding. The seed from plants that arise from haploid culture have the genes to perpetuate the system, therefore, second-cycle selection should allow further accumulation of favorable genes, while imposing stipulations on combining ability. Narrowing of the germplasm base should not be of concern. Genes controlling anther or isolated microspore culture ability have been shown to have a component of dominance. This allows the infusion of conventionally derived elite germplasm into the system. A savings in time of from 1 to 2 years in the development of these inbred line equivalents (doubled haploids) is an advantage of this invention. Shortening the development cycle of elite inbreds permits anther or isolated microspore culture technology to make a useful contribution to commercial breeding programs and to be of great practical importance.

BRIEF DESCRIPTION OF THE DRAWINGS

Other objects and advantages of the invention will become apparent upon reading the following detailed description and upon reference to the drawings in which:

FIG. 1 shows that maize tassels with uninucleate spores are placed at 10° C. for 4 days in the dark. Step 1, around 300 anthers are floated on 3 ml of 0.3M mannitol at 10° C. for 10 to 14 days. Step 2, anthers are chopped with a razor blade to release the microspores. Step 3, anther fragments are filtered out and microspores collected in the filtrate. Step 4, microspores are spun down and washed 3 times. Step 5, microspores are pipetted onto nylon rafts with about 7 to $8 \times 10^4$ microspores per dish and incubate for 2 weeks at 30° C. Step 6, transfer nylon raft with embryoids onto solidified medium for maturation.

FIG. 6B: Transfer of 10 μm nylon raft carrying microspores to another solution.

DESCRIPTION OF THE PREFERRED EMBODIMENT

Figure 1:
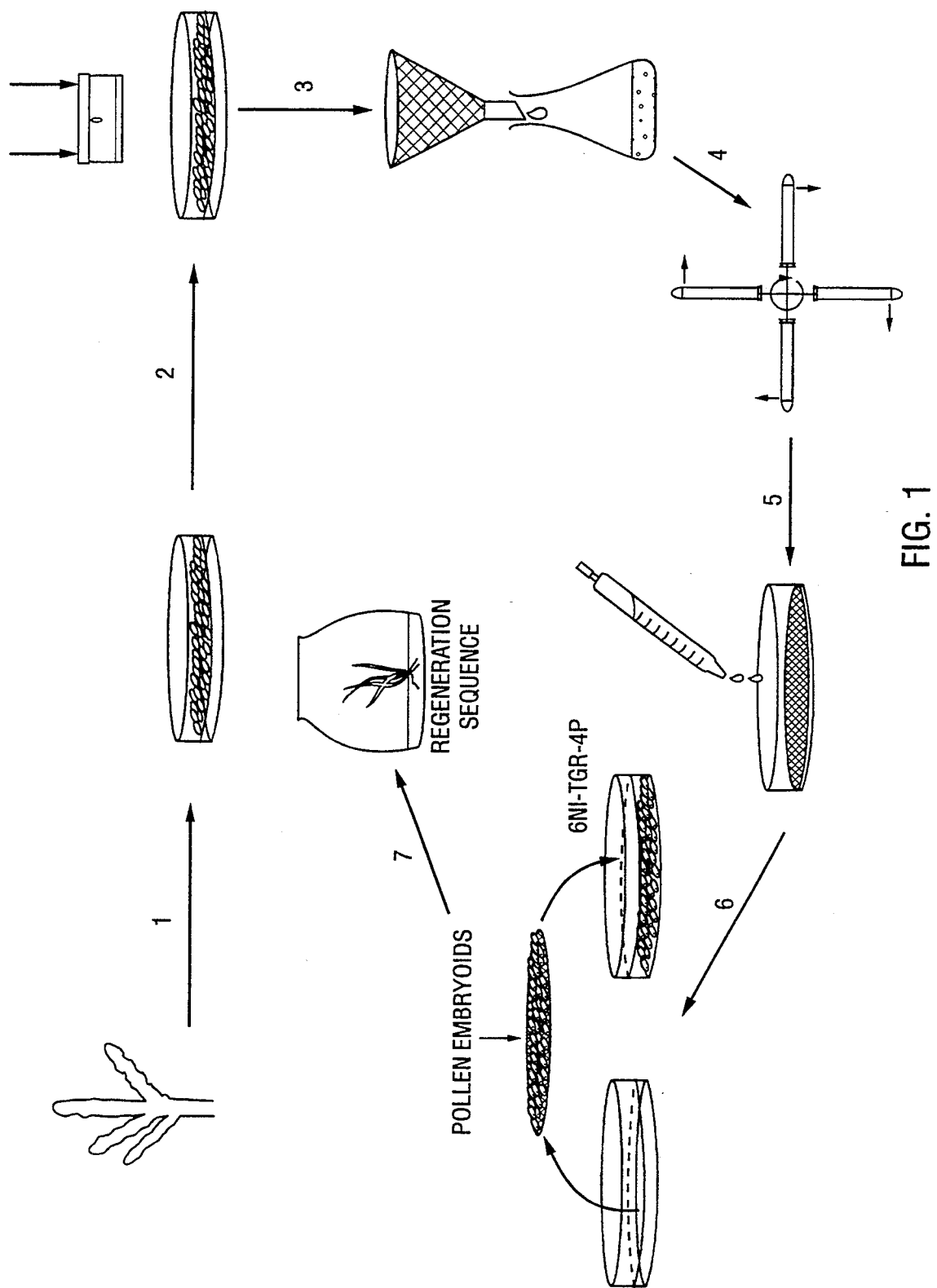
FIG. 1: A diagram of the steps in the production of regenerating plants from isolated microspore cultures. Actual photographs of embodiments of these methods are presented in FIG. 3A, FIG. 3B, FIG. 4, FIG. 5, FIG. 6A, FIG. 6B, FIG. 7, FIG. 8A, FIG. 8B, FIG. 9A, FIG. 9B, FIG. 10A, FIG. 10B, FIG. 11, FIG. 12A and FIG. 12B.

Crops such as corn, wheat, rice and barley are major foci for development of new techniques for the introduction of commercially desirable traits such as drought resistance. An example of this is maize or corn (monocots L.) which is a member of the grass family placed in the tribe Maydeae with a diploid chromosome number of $2n=2x=20$. Maize was domesticated by prehistoric plant breeders to the point where it cannot survive and reproduce in its present form without the aid of man. While maize evolved as a crop of the Americas, it now is grown around the world, having today become the third most important food grain, following closely after wheat and rice.

The concept of maximizing crop yields through the exploitation of heterosis or hybrid vigor was conceived by the maize breeder. Charles Darwin in 1876 reported on the loss of vigor through inbreeding or self-fertilization in this normally cross-pollinating species. He also remarked on the vigor of the progeny resulting from the cross of two self-fertilized plants. W. J. Beal at Michigan followed up Darwin's work from 1877 to 1882 and crossed open-pollinated varieties. He found that yields of the hybrids exceeded those of the parents by 40%. From Beal's work, E. M. East at the Connecticut Experiment Station and G. H. Shull at Cold Spring Harbor, working independently, each unaware of the other's work, developed the concept of developing pure breeding lines of maize through several generations of inbreeding in order to fix phenotypic traits. In 1908 both observed that certain of the $F_1$ hybrids produced yields that were superior to the best open pollinated varieties, with the added feature of crop uniformity, which is important for mechanized harvest. Commercial seedsmen of the time felt that the concept was impractical, because seed returns from inbred seed parents were so poor. Then in 1918, D. F. Jones at the Connecticut Experiment station reported that the double-cross or four-way-cross hybrid showed only a slight yield reduction over the single-cross $F_1$ hybrid, but provided ample seed to insure good profit margins for the seed producer. Thus hybrid maize became a commercial reality.

The morphological structure of the staminate and pistillate inflorescences in maize, and the way in which they are spatially separated from each other, makes this species well suited to controlled self- and cross-pollinations. This unique feature of the plant is of importance from both a commercial standpoint (i.e., hybrid seed production) as well as from one of basic research.

One of the goals of the plant breeder is to find new methods to identify elite progeny resulting from the self-pollination of segregating heterozygous material. Traits of interest are generally quantitative in nature and controlled by many genetic loci. Sophisticated statistical approaches developed by quantitative geneticists have found favor with the maize breeder as a method for improving the mean value of the population. The very practical pedigree method of crossing two or more elite lines and self-pollinating them to increase homozygosity while selecting for improved combining ability is still the most utilized approach. Efforts to streamline the pedigree breeding method have resulted in the development of the single seed descent protocol as well as haploid breeding methods. The latter methods comprise microspore culture, either using anthers or isolated microspores.

Haploid breeding methods refer to in vitro culture of gametophytic cells, the objective being to produce intact, fully fertile, plants. Haploids can be regenerated from both male and female gametophytic cells through the culture of anthers, microspores, ovaries and ovules. Response is measured in the number of embryo-like clusters of cells, and the number of plants regenerated from the cultured haploids. These methods have the advantage of speeding up the process of plant improvement. Commercial breeding is a highly competitive venture wherein an advantage of a year or two can be decisive. The inventors have developed new methods to regenerate fertile plants from anther or isolated microspore cultures. These methods consist of combining certain combinations of stress inducers including cold temperatures with improved culture and subculture protocols. These methods are presented in the following sections and examples.

The mainland Chinese scientists (Anon, 401 Research Group 1975) reported the successful anther culture of maize. Anthers containing microspores at the middle to late uninucleate stage were cultured on MS basal medium (Murashige and Skoog, 1962) with a 12–24% range of sucrose. The frequency of a positive growth response was only near 1%, where a response was defined as a macroscopic embryoid or callus growing out of an anther. A callus is an aggregate of cells. There are at least two types of calli: one made up of heterogeneous late embryogenic tissue (Type I); the other loose, friable and capable of differentiation into embryoids in culture (Type II). Embryoids may also arise directly from pollen. An embryoid is an aggregate which exhibits recognizable embryonic structures. Embryoids may exhibit variations in morphology. Some may go through all the developmental stages characteristic of natural embryogenesis, others may exhibit abnormal development, e.g., one or more fused scutellar bodies. Mutants, e.g. albino plants, may arise. Mutants may be desirable or undesirable from a commercial standpoint, depending on their phenotypic effects.

Two additional reported successes in maize anther culture came from Chinese laboratories in 1978. One was by Miao et al. 1981 with a 7% frequency of response when they used N6 basal medium (Chu 1981) with 12% sucrose, 0.5% activated charcoal, and 500 mg/l casein hydrolysate. The plant growth regulators were 2 mg/l 2,4-dichlorophenoxyacetic acid (2,4-D) and 1 mg/l kinetin. A second article was by Ku et al. 1981, where they reported a 13.1% frequency of response using a Yu-pei (YP) basal medium with 0.5% activated charcoal, 500 mg/l lactalbumin hydrolysate, and 12% sucrose. The growth regulator added was 0.1 mg/l 2,4,5-triiodobenzoic acid (TIBA), an antiauxin. Kuo et al. (1985) gives a detailed account of the identification of important variables necessary for the successful anther culture of maize by Chinese scientists. Media components believed necessary for good levels of response were: high sucrose concentration, activated charcoal, and organic nitrogen.

Confirmation of corn anther culture outside of China was belated but several reports were published in 1981 and 1982. Each of these reports was dependent on obtaining responsive germplasm from China. One was by Nitsch et al. 1982, who reported response rates between 3% and 10%. They used either N6 or YP basal salts with 500 mg/l casein hydrolysate, 0.5% activated charcoal, and 0.1 mg/l TIBA. Unlike the Chinese, they found 6% sucrose (not 12%), as well as the addition of proline at 100 mg/l, important to optimize responsiveness. Nitsch's group used a cold pretreatment of 7 days at 14° C. They also reported that incubation of cultures under red fluorescent lights gave the best levels of response. Other confirming reports were by Brettell et al. (1981) and Genovesi and Collins (1982). Additional points of interest in the work of Genovesi and Collins were (1) the identification of responsive U.S. germplasm; and (2) the use of a 14-day, 8° C. cold pretreatment.

The effect of donor plant physiology and vigor on anther culture response frequency have been explored (Nitsch et al. 1982). Environmental factors which have been reported to influence donor plant vigor include photoperiod, light intensity and quality, as well as temperature, and nutrition.

Investigators do not agree on the most responsive developmental stage for corn anther culture. Some indicate that the uninucleate microspore is the most responsive stage for culture. Some have shown a preference for the mid-uninucleate stage, while others prefer the late uninucleate stage. The mid-uninucleate stage is the developmental stage of the microspore when the nucleus is situated in the center of the cell before the formation of a vacuole. The late uninucleate stage is described as the point in time when the nucleus has migrated to a position next to the cell wall opposite the germination pore, with a well-formed vacuole. The inventors have found the uninucleate stage to be preferred.

In addition, there is no agreement on environmental conditions conducive to anther response. An anther response is defined as the normal proliferation of one or more embryoids or calli from microspores contained in the anthers. Plated anthers incubated at temperatures in the range of 25° to 28° C. generally respond in 4 to 6 weeks. Some investigators carry out this phase of culture totally in the dark (Ting et al. 1981), while others culture 1 to 2 weeks in the dark then move to a 16-hr photoperiod under white fluorescent lighting (40 µE $m^{-2}s^{-1}$) (Genovesi and Collins 1982; Petolino and Jones 1986). Three reports describe media which have been used for the cloning of somatic tissues of elite maize germplasms (Duncan et al. 1985; Close and Ludeman 1987; Sletten and Tomes 1987) and may have some utility in cloning androgenic embryoids.

The inventors have found the solution to some of the confusion regarding anther response variation. They have found that responsiveness in culture is not just a function of the microspore stage of development, but also of the developmental state of the anther wall. Two classes of anthers, both at the mid-uninucleate stage of development, have been observed. When anthers were cold shocked for 14 days prior to introducing them into culture (Genovesi and Collins 1982), one class of anthers, when removed from the cold, became puffed in appearance, light yellow, and easily dehisced their contents when touched with forceps. This class of anther has a poor frequency of response. The second class of anther, when removed from cold pretreatment, appears deep yellow to orange, long, thin, and crisp, with no indication of puffiness. This class of anthers is the most responsive.

COMPOSITION OF MEDIA

Basal Salts

Although many people have explored various media compositions to determine the optimum conditions for haploid cultures, there is still no consensus on this complex issue. Various basal salts media have been used to nourish dividing maize microspores in anther cultures. They are: N6 (Miao et al. 1981; Nitsch et al. 1982; Brettell et al. 1981); Yu-pei (or more recently Yu-bei), designated as YP (Ku et al. 1981; Nitsch et al. 1982; Genovesi and Collins 1982; Pauk 1985; Petolino and Jones 1986; Dieu and Beckert 1986); Zheng 14 (Ting et al. 1981; Dieu and Beckert 1986); and finally 6M1, a designation given it because the ratio of nitrate to ammonium nitrogen is 6:1 and the originator of the medium did not name it (Miao, 1980). Miao's work with nitrogen ratios was done using an MS basal salts medium. The same nitrogen ratio can be utilized in an N6 basal salts medium and is such a modification by the inventors coded as 6N1. The inventors have modified the basic compositions proposed for media and find particular advantages in the media defined in Example 6. Illustrations of the rationale for some of the inventor's improvements are presented also.

Charcoal

Numerous organic additives to the various media have been proposed. The inventors find that 0.5% activated charcoal improves response levels. Beneficial effects of activated charcoal are believed due either to the absorption of toxic substances excreted by the anther wall or the absorption of toxic media components or metabolites.

Sucrose

There is great confusion about the optimum range for sucrose in media. An array of sucrose concentrations have been proposed: starting with 6% (Nitsch et al. 1982), 9% (Tsay et al. 1986), 12% (Ku et al., 1981; Miao, et al., 1981; Dieu and Beckert, 1980), and 15% (Ting et al. 1981). In a statistical test for significance performed by the inventors, 6% sucrose was compared to 12% as part of a four-factor Randomized Complete Block (RCB) design. For each of the two sucrose levels, 13,440 anthers were cultured. Anthers on 12% sucrose responded with a frequency of 5.35%, while those on 6% sucrose responded with a frequency of 2.25%. The 12% sucrose level was significantly ($\alpha=0.05$) better than 6%.

Nitrogen

Contrary to previous reports of the importance of an organic nitrogen source in anther culture media, e.g., for barley cultures (Olsen, 1987), the inventors have, as a part of a four-factor RCB design, made a comparison of various organic nitrogen sources and found that no organic nitrogen at all proved to be as effective as the organic supplement of 100 mg/l proline plus 400 mg/l casein hydrolysate. The latter is believed to be a nitrogen source that gives good response. However, proline may be of some benefit, because it nullifies the negative effects of casein hydrolysate observed when casein was included singularly as an additive.

Hormones

There has been no consensus on a requirement for hormones at various stages. Miao et al. (1981) supplemented an N6 basal medium with 2 mg/l 2,4-D and 1 mg/l kinetin to achieve maximum levels of anther culture response at 7%. Ting et al. (1981) supplemented a Zheng-14 basal medium with 2 mg/l 2,4-D, 1 mg/l 6-benzylaminopurine (BAP) and 1 mg/l α-naphthaleneacetic acid (NAA) to achieve an optimum response level of 17%. Ku et al. (1981) compared anther response levels of a YP basal medium supplemented 2 mg/l 2,4-D, 1 mg/l kinetin and 2 mg/l BAP versus YP supplemented with various levels of the antiauxin, TIBA (i.e., 0.05, 0.1, and 0.5 mg/l). Response levels were in general better on the TIBA-supplemented medium and a maximum response frequency of 13.1% was achieved with a 0.1 mg/l concentration. Dieu and Beckert (1986) have compared anther response levels on Zheng-14 supplemented with 2,4-D, BAP, and NAA, at the levels previously mentioned, with YP plus 0.1 mg/l TIBA. They found the latter to perform significantly better. Pescitelli et al. (1989) derived some plants from anther cultures using an N6 medium supplemented with dicamba and 2,4-D. What the inventors have found is that hormone additives in the maturation and regeneration media promote root and shoot initiation. Embodiments are shown in Example 6 which presents maturation and regeneration media comprising TIBA, BAP, NAA and 2,4-D.

Ethylene Action Inhibitors

Increased frequency of plant regeneration from maize callus cultures was found when ethylene action inhibitors were added to callus culture media (Songstad et al., 1988) confirming suggestions of Vain et al., 1989. Examples of these inhibitors are norbornadiene and silver nitrate. Silver nitrate is preferred in premature and embryoid/callus inducing media. The inventors have found $AgNO_3$ effective and propose that its addition to media, or that of a similar inhibitor, facilitates regeneration.

Vitamins

Various vitamins at differing levels have been tested by the inventors. Vitamins comprise glycine, thiamine, pyridoxine, nicotinic acid, inositol, and pantothenate. The inventors find that thiamine and nicotinic acid are beneficial for the induction of good levels of response. Conversely, pyridoxine, inositol or pantothenate appear to depress anther responsiveness.

Solid-Based Media

The inventors have found that maize anthers plated on an agarose-based medium responded significantly better with a frequency of 13.51% compared to those on agar (8.33%). Examples of agarose-based media is shown in Example 6, the maturation and regeneration media formulas. Gelrite was as effective as the more expensive agarose. Phytogel may also be used.

GENOTYPE

Anther culture responsiveness in corn varies with the genotype of the source plant. Many genotypes respond to culture, however, there is variation in response among genotypes. To select source plants from a series of lines that will show the highest frequencies of response, conventional breeding from ancestral lines with commercially desirable traits, followed by laboratory screening for embryoids or regenerated plants may be performed. Although the methods for production of plants from haploid cultures disclosed herein are applicable to all permissive genotypes, some will respond better than others. These lines may then be selected as parents to further concentrate permissive genotypes into certain germplasm. This may further increase response rates.

With experience gained from working with the Chinese germplasm, researchers have identified genotypes in the United States (Genovesi and Collins 1982; Petolino and Jones 1986) and European genotypes (Dieu and Beckert 1986) with similar good levels of responsiveness.

The genetics of in vitro haploid culture response are not clear. Results of various genetic studies indicate that it should be possible to breed for improved anther culture responsiveness through several cycles of selection. The well established phenomenon that inbreeding in maize results in loss of vigor or inbreeding depression is correlated with a corresponding loss of responsiveness according to some reports. The inventors have found $F_1$ hybrids respond more frequently than their component inbreds (Genovesi and Collins 1982; Dieu and Beckert 1986), suggesting a dominant genetic factor or factors. In contrast, Pace et al (1987) found that an inbred line responded at a higher rate than the $F_1$ hybrid resulting from a single-cross wherein that inbred was a parent. It is likely that many genes control responsiveness and that their frequencies vary among lines.

To obtain source plants for culture of anthers or isolated microspores, germplasm descended from public lines with commercially desirable traits are preferred. For corn, public line "Stiff Stalk Synthetic" (SSS) is preferred. $F_1$ hybrid plants are produced by conventional breeding techniques using as parents, plants that are characterized by commercially desirable traits such as high ear yield or drought resistance. Examples of such descendent lines of SSS are B14 and B73. If genes are identified that affect in vitro response, those would be desirable to incorporate into the crosses. However, following the methods disclosed herein, lines that respond well in culture have been successfully selected in the absence of identifying specific genes for responsiveness, by conventional breeding of stocks derived from SSS to produce $F_1$ progeny.

Plant compositions comprising microspores from those $F_1$ are then screened in the laboratory for either microspore or anther responsiveness. It will not generally be necessary to screen using both assays. Following the methods disclosed herein, such screening can be completed in 6–8 weeks if responsiveness is defined as embryoid production from anthers or isolated microspores. This is probably sufficient screening for permissive genotypes, because embryoids are likely to produce some fertile plants. If it is desired to screen for ability to regenerate plants, then about another two months is required. Batch screening of many inbred lines can be done concurrently. For example, the inventors can screen about 30 lines at a time, and believe 100 could be screened without unreasonable effort.

Of those genotypes screened, the most responsive may be selected as plant source lines for haploid culture. About 2 or 3 of the best lines out of about 30 are generally selected. Following this protocol, the inventors have developed useful lines for anther and isolated microspore culture, e.g. G238, G138, G289.

COLD-SHOCK PRETREATMENT OF MICROSPORES

Cold-shock pretreatment of developing microspores has been investigated by the inventors in a variety of settings. Through these studies, the inventors found cold stress to aid in switching the genetic program from development of a gametophyte to development of a sporophyte.

In an effort to further clarify these data, the inventors performed a statistical analysis with seven cold-shock pretreatment conditions (Table I). The best response level of 7.47% was achieved with a 14-day 10° C. cold pretreatment.

TABLE 1

Effect of cold-shock pretreatment of tassels on anther culture responsiveness.

| Cold pretreatment[a] | % Mean response[b] |
|---|---|
| 14 days 10° C. | 7.47a |
| 14 days 8° C. | 5.96a |
| 7 days 4° C. + 7 days 8° C. | 4.27b |
| 21 days 8° C. | 2.29bc |
| 7 days 14° C. | 2.37cd |
| 7 days 10° C. | 2.37cd |
| None (control) | 1.22d |

[a]For each cold-pretreatment condition 3840 anthers were cultured.
[b]Means with the same letter are not significantly different at $\alpha = 0.05$.

The inventors concluded that 14 days at 10° C. with ranges from 8° to 10° C. at 14 days or from 4° to 8° C. at 7 days produced good results.

GROWING REGENERATED PLANTS TO MATURITY

After a response becomes obvious to the naked eye (1 to 1.5 mm of a cell aggregate), the aggregate is moved to a medium with reduced sucrose (2–3%) and no activated charcoal. One of two courses of action can be taken at this point: (1) to germinate the embryoids directly into plantlets, or (2) to induce totipotent calli from which several clonal regenerates can be derived. Numerous media have been described for the direct germination of embryoids. The best of these promoted the germination of only 10 to 20% of the embryoids into plantlets (Dieu and Beckert 1986; Petolino and Jones 1986). The alternate approach is to initiate totipotent calli from haploid embryoids. Because genotype and developmental state of the embryoid may drastically influence the success with which totipotent cultures may be induced, an array of media formulations was tested.

The inventors have found that, after a well defined shoot and root system have been established on the regenerated plantlet, it is ready to be transferred to a 10-cm clay pot. Shoots are characterized by good whorl formation obvious to those skilled in the art. A germination mix consisting mostly of shredded peat moss may be used. Transplanted regenerates are preferably kept for several days at a high humidity (approximately 70%) to allow them to develop a waxy cuticle (or harden off). When it becomes obvious that active shoot growth has been initiated, the transplant is generally put in a 25-cm pot containing an all-purpose potting soil, and fertilized with a time-release fertilizer such as Osmocote ®.

The tissue culture process imposes a stress on the regenerated plantlet, the effects of which may be manifested during the vegetative phase of growth and flowering. Regenerated plants may exhibit one or more developmental abnormalities including lack of tassel or ear development, tassel seed, complete transformation of the tassel to a terminal ear, and asynchronous pollen shed and silk emergence (Miao et al. 1981; Petolino and Jones 1986). Similar abnormalities result when field-grown plants are exposed to toxic levels of herbicides. Some genotypes are more sensitive to damage by certain classes of chemicals than others. One might expect the same to be true for developmental abnormalities arising from the exposure of totipotent tissue to growth regulators in vitro. Some genotypes are less affected, and should thus be preferentially used. In previous results, most plants returning seed appeared to be haploid/diploid chimeras with fertile sectors in the tassels and ears. Of those, only an occasional plant was completely fertile, that is, produced full ears.

The haploid chromosome complement may be doubled to produce a diploid complement by various doubling agents. (Jensen, 1974). Wan treated anther culture derived plant calli with colchicine and reported diploidy induction. (Wan, et al. 1989). With doubling of chromosomes by the methods disclosed herein, their objective being to produce non-chimeric diploids, full ears are more frequent. Growth environment of the regenerated plant may also affect the frequency of successful self-pollinations. Haploid/diploid chimeric plants do not cope well with the natural environment. In the inventors' experience, regenerated plants grown from April through July in the protected environment of the greenhouse were about twice as likely to be self-fertilized as regenerates transplanted to the field.

ISOLATED MICROSPORE CULTURES

Isolated microspore culture techniques face similar hurdles to those described above for anther cultures, and many of the proposed solutions are similar. Attempts to culture isolated microspores have generally not been successful (Keller et al., 1987). In most reports, efficiency of callus formation or embryogenesis in mechanically isolated microspores is reduced in comparison to anther culture systems.

The present invention relates to improvement over previous methods. The inventors have produced higher response rates than those previously reported by using a combination stresses, for example, cold temperatures and pretreatment with an environment which diverts the microspores to an embryogenic pathway, possibly by inducing starvation. An embodiment of such an environmental factor is a non-aldose, non-ketose, 3–6 carbon sugar with a $CH_2OH$ at the terminus. Mannitol is such a factor. Other aspects of the invention are the use of a doubling agent and a support for microspores. Stress factors such as mannitol and colchicine are preferably used in the preculture stage. Examples of these methods are presented as follows:

EXAMPLES

EXAMPLE 1

Production of "Permissive" Genotype for Anther or Isolated Microspore Cultures

"Permissive" genotypes are those that respond to manipulation of the in vitro tissue culture environment yielding callus/embryoids which are capable of regenerating into entire plants, more specifically, fertile plants.

To obtain a permissive genotype, an $F_1$ hybrid line is produced by crossing two elite inbred lines. Elite lines are pure breeding inbreds with commercially valuable traits resulting from classical breeding methods. The crosses are made using methods well known to those of ordinary skill in the art. The elite inbred parental lines are selected from either public or private (proprietary) lines. For this invention, two preferred parental lines were derived from an ancestry which includes the well-known, publicly available "Stiff-Stalk Synthetic", an important commercial corn breeding resource.

In producing permissive genotypes in corn, descendents of the "Stiff-Stalk Synthetic" population are useful. These include lines designated B14, B37, and B73 and the like. The B14 line is ancestral to parental lines used by the inventors to produce $F_1$ hybrid. One of these is designated G238, another is G138. Descendants of the B14 line have genotypes amenable to anther culturing. B73 is another descendent of the Stiff-Stalk Synthetic that is public and may be used as a parent to produce permissive genotypes by classical breeding techniques without undue experimentation. Through these types of manipulations, useful lines such as G238, G138, G239 have been developed.

EXAMPLE 2

Regeneration of Fertile Plants from Anther Cultures

Tassels containing uninucleate microspores were pretreated for 4 days at 10° C. Anthers from surface sterilized tassels were then dissected out of tassels and floated on a media comprising 0.3 M mannitol and 50 mg/l ascorbic acid. 3 ml of this solution was placed in a 60 mm petri dish. The anthers were incubated for 10 days at 10° C. Anthers were isolated from about 120 tassel spikelets. After preculture on mannitol, about 24 anthers were placed in each 100 mm dish containing 30 ml of 6N1-TGR-P4 and incubated in the dark at 30° C.

After a period of 21 days, callus and embryoid formation was observed. Embryoids exhibiting recognizable embryo-like structures were selected by visual inspection and subcultured to new dishes comprising a series of regeneration media. The first regeneration medium employed was designated CMP¼+¼ (the alternate code is 1511, see Example 6 for ingredients.) Incubation was at 28° C. for 14 to 21 days.

After shoots were observed, plantlets were subcultured to a root initiation media (designated 3N¼ or 1505). (See Example 6 for ingredients.) Incubation was at 28° C. for 14 to 21 days. After roots were observed to be initiated the plantlets were transferred to a finishing medium (designated 3S6PICAN or 1519, see Example 6 for ingredients). Robust plantlets were transplanted to soil in 4" pots for further development.

Of the 1000 anthers cultured, 30% yielded callus or embryoids. Of the 100 embryoids selected for germination and plant regeneration, 16.67% yielded plants, 25% of which were fertile.

EXAMPLE 3

Inducing Diploidy in Plants Regenerated from Anther or Isolated Microspore Cultures To induce the haploid chromosome complement of microspores to become diploid, the steps in the anther culture procedures of Example 2 wherein anthers were floated on a 0.3 M mannitol+50 mg/l ascorbic acid (3 mls in a 60 mm dish, for 10 days), were modified by adding colchicine, a chromosome doubling agent, to the float solution. Experiments were run, each with either 0.01, 0.025, 0.05 or 0.1% concentration of colchicine. Pretreatment of the tassel was at 10° C. for 4 days, then 10 days or 11 days on the mannitol and colchicine preculture medium. Uninucleate cells increase in frequency as the spindle is inhibited. Results of these are in Table II using this indirect assay.

TABLE II

Percent of Uninucleate and Binucleate Microspore Divisions Induced by Colchicine.

| % Colchicine | % Uninucleate | % Binucleate |
|---|---|---|
| Experiment A: | | |
| 0 | 14 | 86 |
| 0.01 | 21 | 79 |
| 0.05 | 74 | 36 |
| Experiment B: | | |
| 0 | 16 | 84 |
| 0.01 | 25 | 75 |
| 0.025 | 66 | 34 |
| 0.05 | 70 | 30 |
| 0.1 | 60 | 40 |

EXAMPLE 4

Use of a Support for Cultured Cells

FIG. 1 illustrates a general scheme for the culturing of maize isolated microspores. In step 5, the microspores in suspension are pipetted onto a nylon mesh raft.

Figure 2:
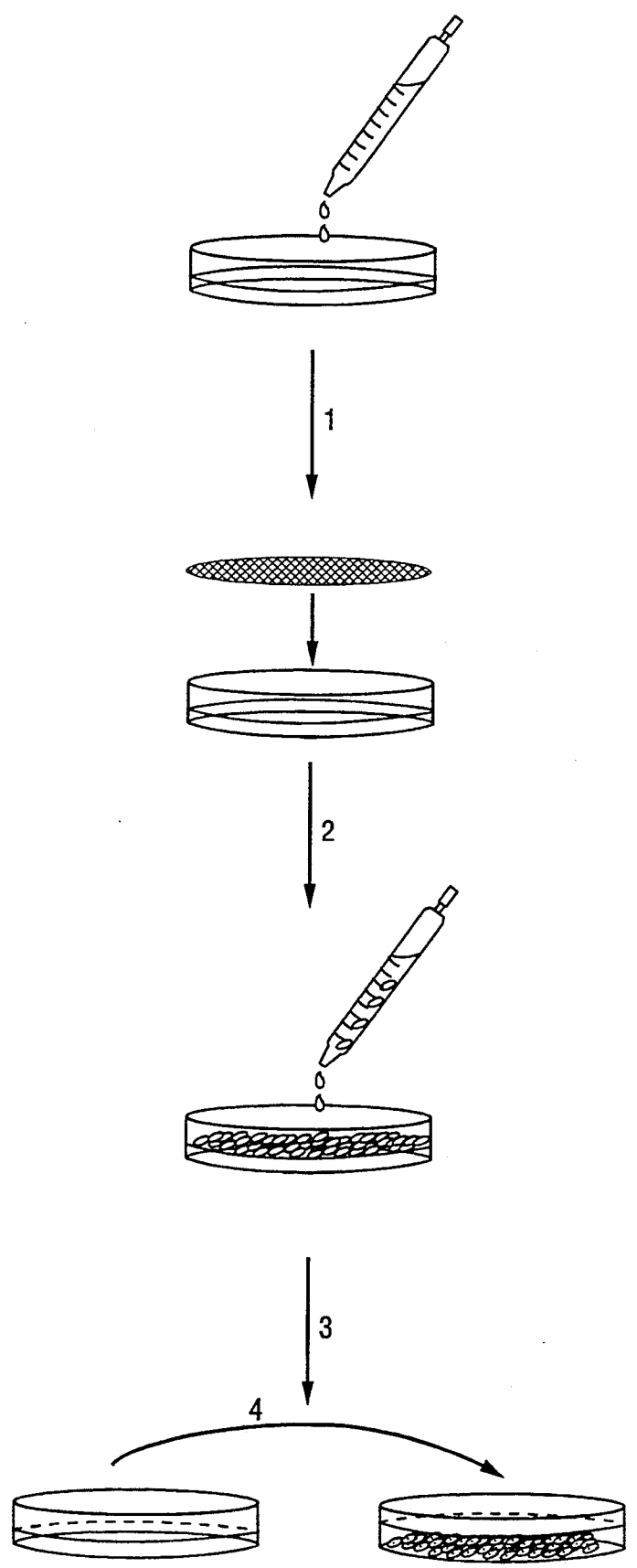
FIG. 2: A diagram of the general method to initiate a culture with a solid support, to produce embryoids/calli. In this figure, a nylon raft is shown onto which are pipetted microspores in suspension. Step 1, pipette in 1.2 ml of "D" medium into a 60 mm petri dish. Step 2, introduce a 10 μm nylon raft, around 55 mm in diameter. Surface tension of the liquid medium causes it to float. Step 3, pipette 1 ml of suspended microspores at 7 to $8 \times 10^4$ per ml onto the top of the nylon raft. The liquid passes through the mesh and the microspores stay on top. The mesh stays on top of the total volume of liquid medium of 2.2 ml. Step 4, incubate 2 weeks in the dark at 30° C. then transfer raft with embryoids to solid medium.

FIG. 2 shows in more detail the set up of the nylon mesh raft. The nylon raft used in this embodiment was about 55 mm in diameter and with a 10 μm pore size. The raft will float in the liquid medium due to surface tension. Shown in FIG. 2 is 1.2 mls of media in a 60 mm petri dish to which 1 ml of medium-containing microspores is pipetted. The total volume of media in the dish after the suspended microspores are pipetted onto the mesh is about 2.2 mls. The liquid passes through the mesh and the microspores ($7$–$8 \times 10^4$/ml in this example) stay on top.

Microspores were incubated for 2 weeks in the dark at 30° C. then the raft containing embryoids which have developed were transferred to a solid medium, e.g. 6N1-TGR-P4, for maturation.

EXAMPLE 5

Regeneration of Fertile Corn Plants from Isolated Microspore Cultures (see also FIG. 1)

Tassels (FIG. 3A and FIG. 3B) were obtained from corn plants and incubated (pretreated) at a temperature of 10° C. for 4 days.

Figure 3A:
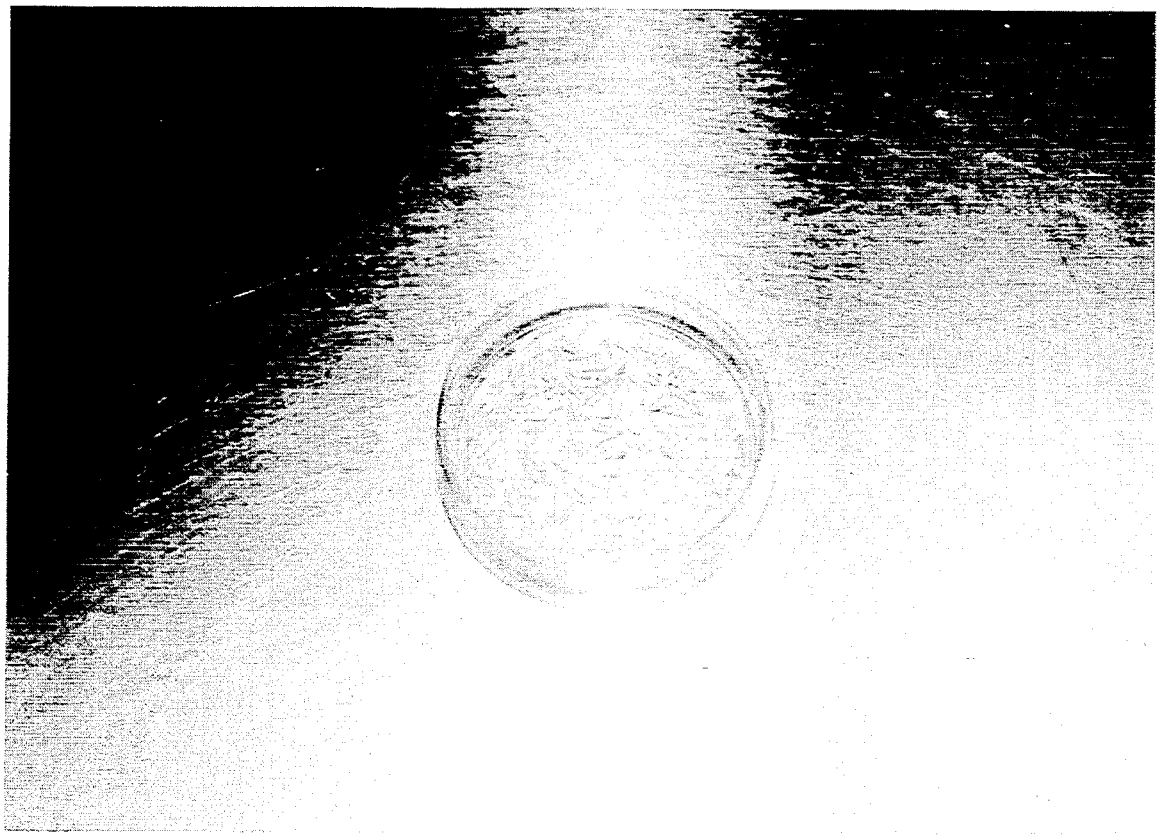
FIG. 3A: Shows a petri dish containing maize tassels which have been pretreated at 10° C. for 4 days.
Figure 3B:
FIG. 3B: shows anthers dissected from the tassels and placed in an isolation media, in this embodiment, a 3 ml solution comprising 0.3 M mannitol. The anthers were incubated at a cold temperature, in this embodiment about 10° C., for a period of from 10–14 days.

After the pretreatment 1, anthers were dissected out of the tassels and placed in 3 ml of a solution of 0.3 M mannitol. About 300 anthers were floated in a 60 mm petri dish. (FIG. 3A and FIG. 3B). The anthers were then incubated in this solution for 14 days at 10° C..

The anthers were then chopped into pieces 2 with a razor blade to release microspores into the medium.

The free microspores were separated from the anther wall debris by passing the mixture through a 112 μm nylon filter 3. The microspores were collected in the filtrate. The microspores were then washed and centrifuged 4 down three times to eliminate toxic compounds created by chopping up the anthers.

Figure 4:
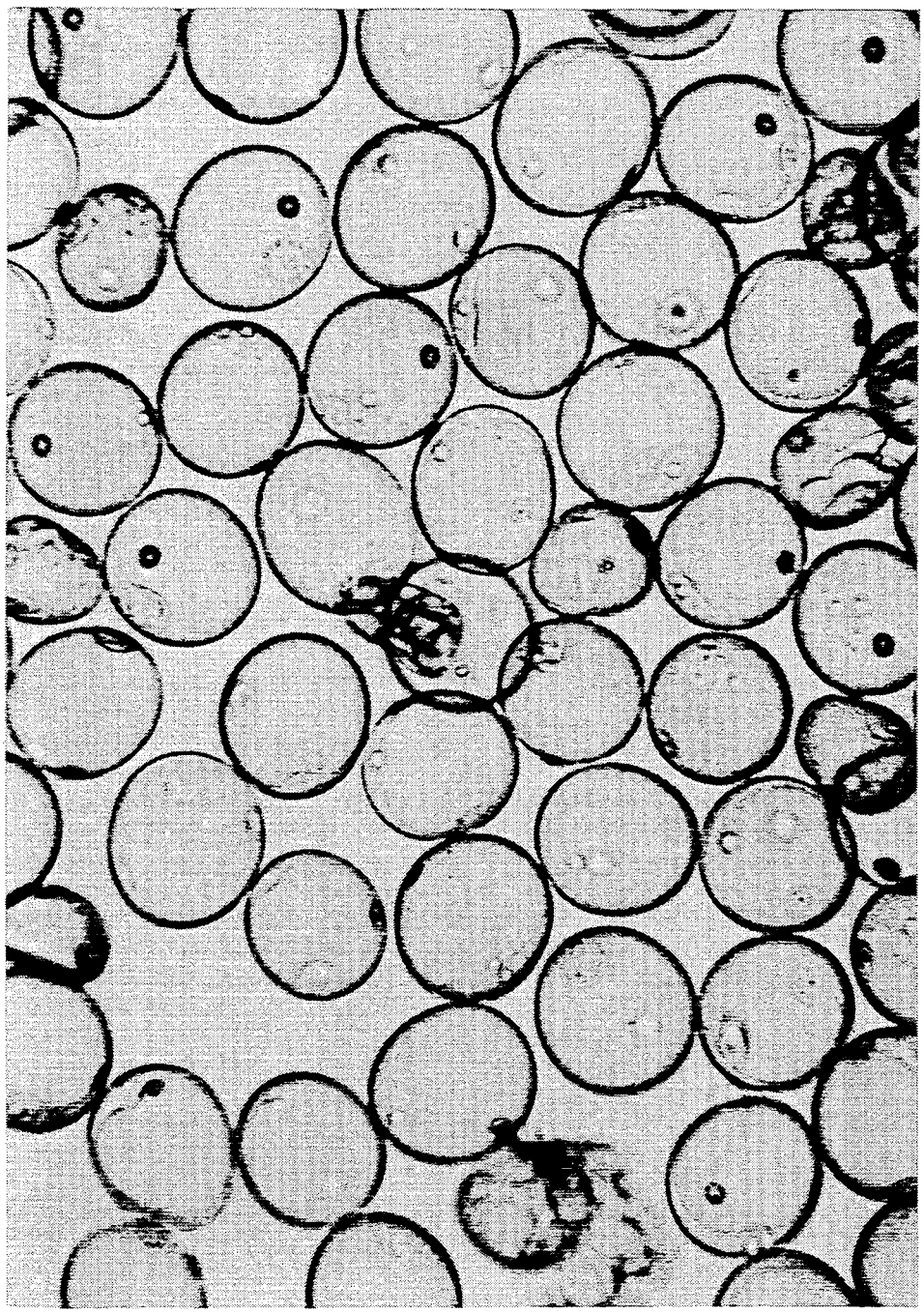
FIG. 4: After the anthers are chopped into pieces with a sharp instrument, in this embodiment a razor blade, free microspores are separated from the anther wall debris by passing the mixture through a filter, in this embodiment a 112 μm nylon filter, then washed and centrifuged. Shown in this figure are free isolated microspores with visible nuclei. Now binucleate, they started as uninucleate microspores prior to mannitol pretreatment.

FIG. 4 is a photograph of a pure preparation isolated microspores. It can be seen that some cells are uninucleate, others are binucleate.

Figure 5:
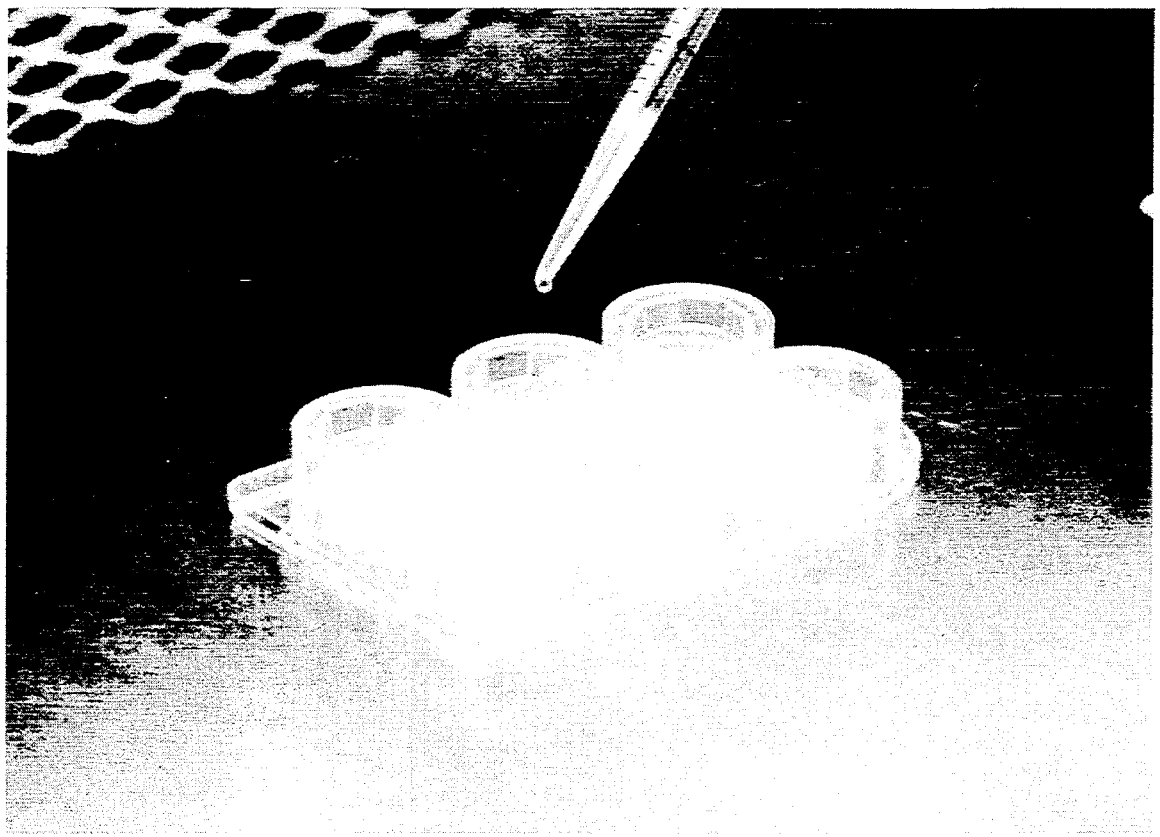
FIG. 5: Isolated microspores are shown being pipetted into a Transwell ® culture dish, an embodiment of a solid support for microspores.
Figure 6A:
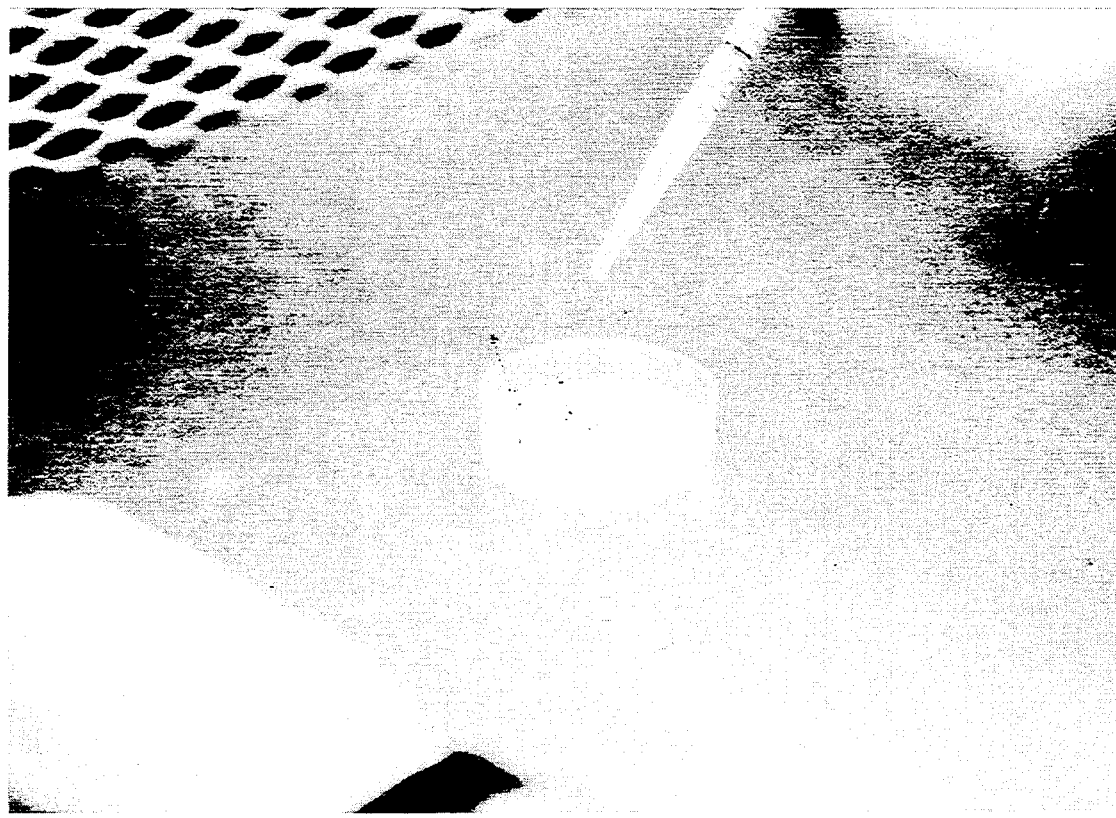
FIG. 6A and FIG. 6B: Isolated microspores in suspension in an isolation media are shown being pipetted onto a 10 μm nylon raft floating on 1.2 mls of medium "D." (See Example 6). The liquid medium passes through the filter while the microspores are held at the medium/air interface and are not subjected to deleteriously low oxygen tension.
Figure 6B:
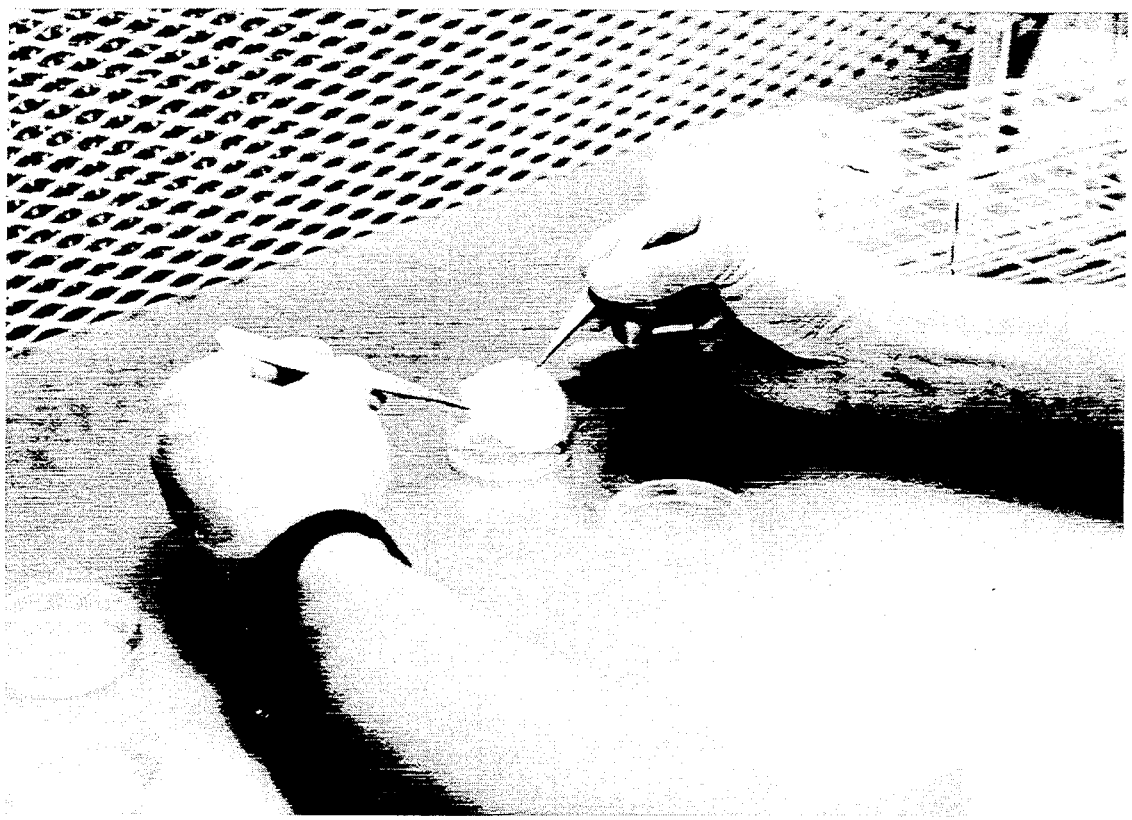

As shown in FIG. 5, FIG. 6A and FIG. 6B, the microspores in suspension were pipetted onto a support 5. FIG. 5 shows pipetting into wells of a Transwell® dish. FIG. 6A and FIG. 6B shows the preferred support, a nylon mesh raft (see also FIG. and Example 4).

One ml of isolated microspores in suspension was pipetted onto a 10 μm nylon raft which was floating on 1.2 mls. of medium "D" (see Example 6). Using the mesh raft as a support, the liquid medium passes through while the microspores are held at the medium/air interface. About $7–8 \times 10^4$ microspores were plated per dish.

Figure 7:
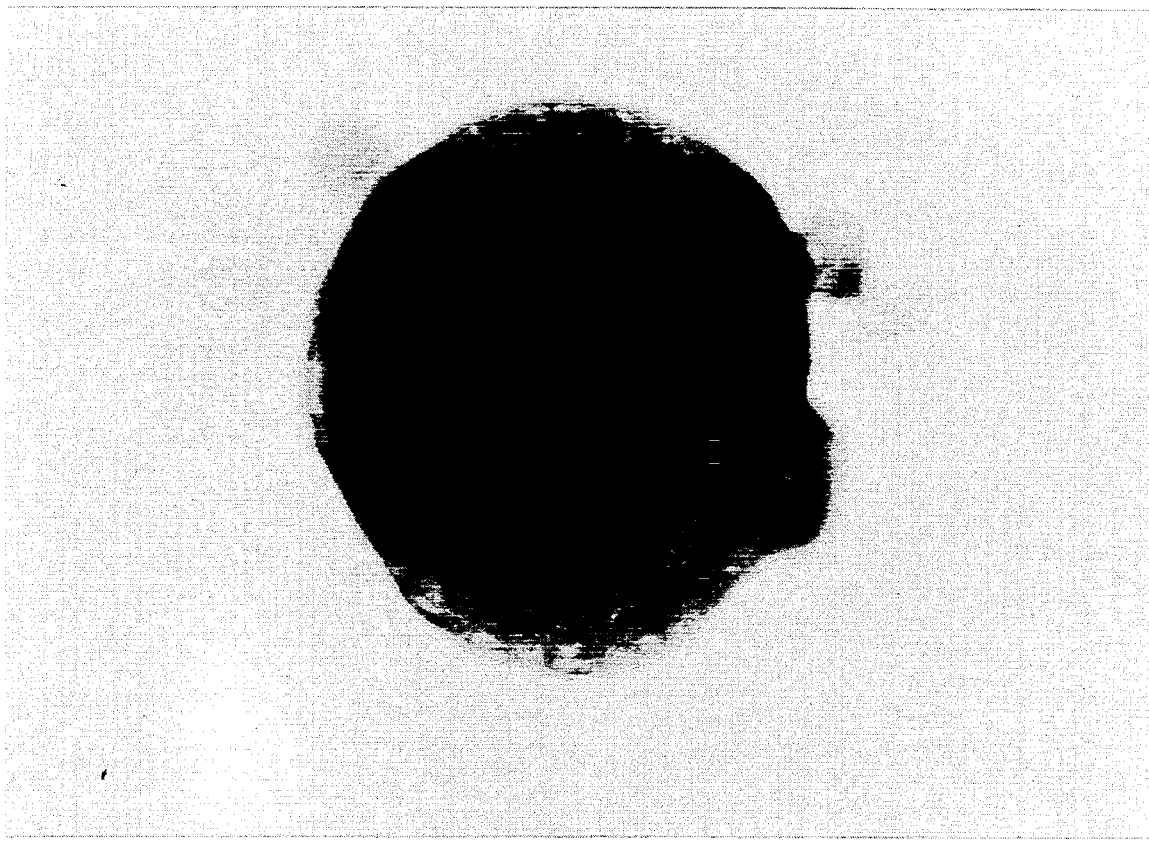
FIG. 7: One of the multicellular structures arising from microspore cultures. Shown is a structure 14 days
Figure 8A:
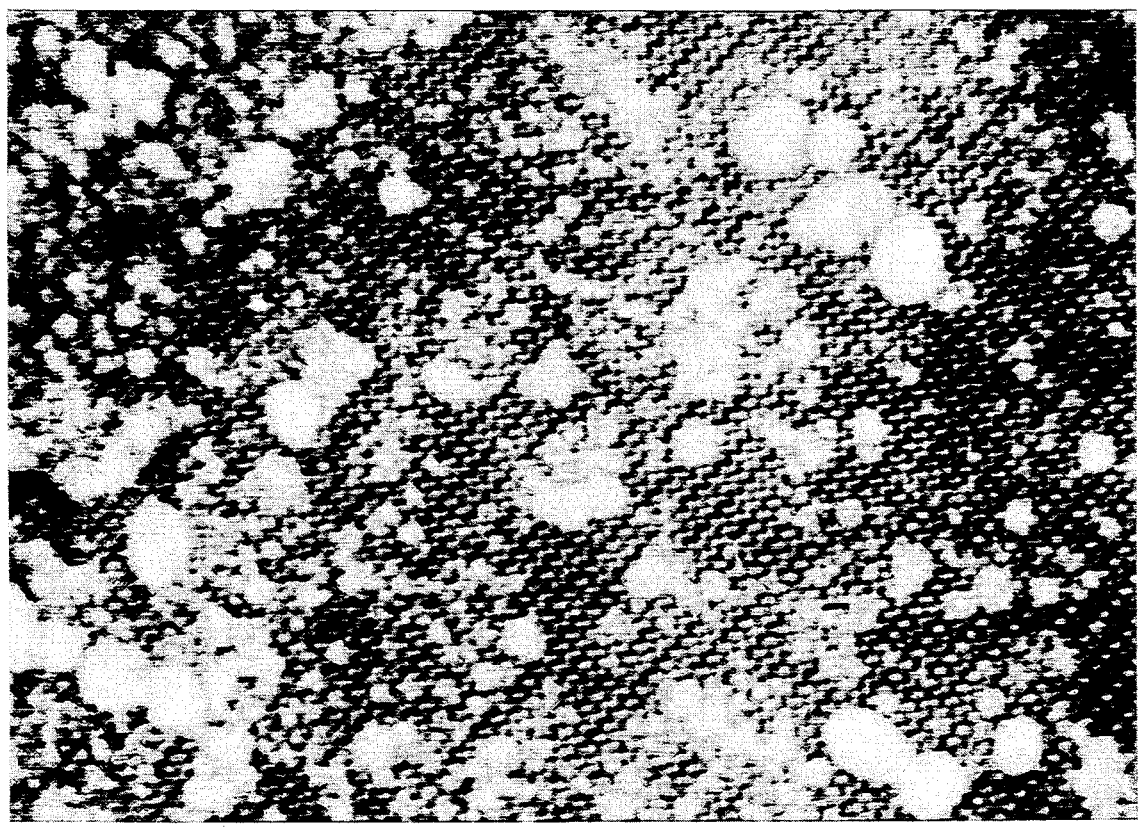
FIG. 8A and FIG. 8B: Calli and embryoids growing on a nylon mesh raft are shown.
Figure 8B:
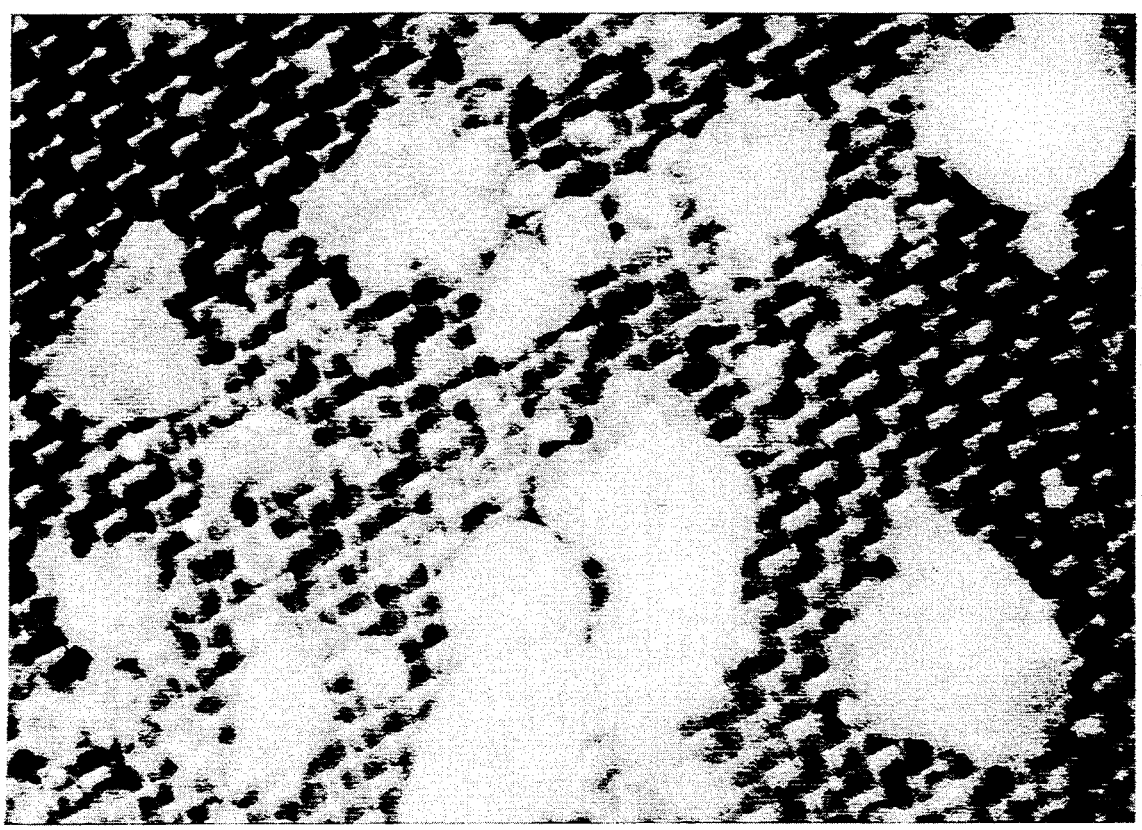

After 14 days of incubation at 30° C., multicellular structures arose from the microspores on the support. FIG. 7 shows an example of such a structure, this one on a bilayer plate support. A bilayer plate has a liquid media atop a solid base. FIG. 8A and FIG. 8B shows calli/embryoids growing on the nylon mesh raft 6. Calli/embryoids developed in medium "D" (see Example 6).

Figure 9A:
FIG. 9A and FIG. 9B: Shown are embryoids which have been transferred to full strength 6N1 medium solidified with Gelrite to permit embryoids to mature. Embryoids are still attached to the nylon mesh raft.
Figure 9B:
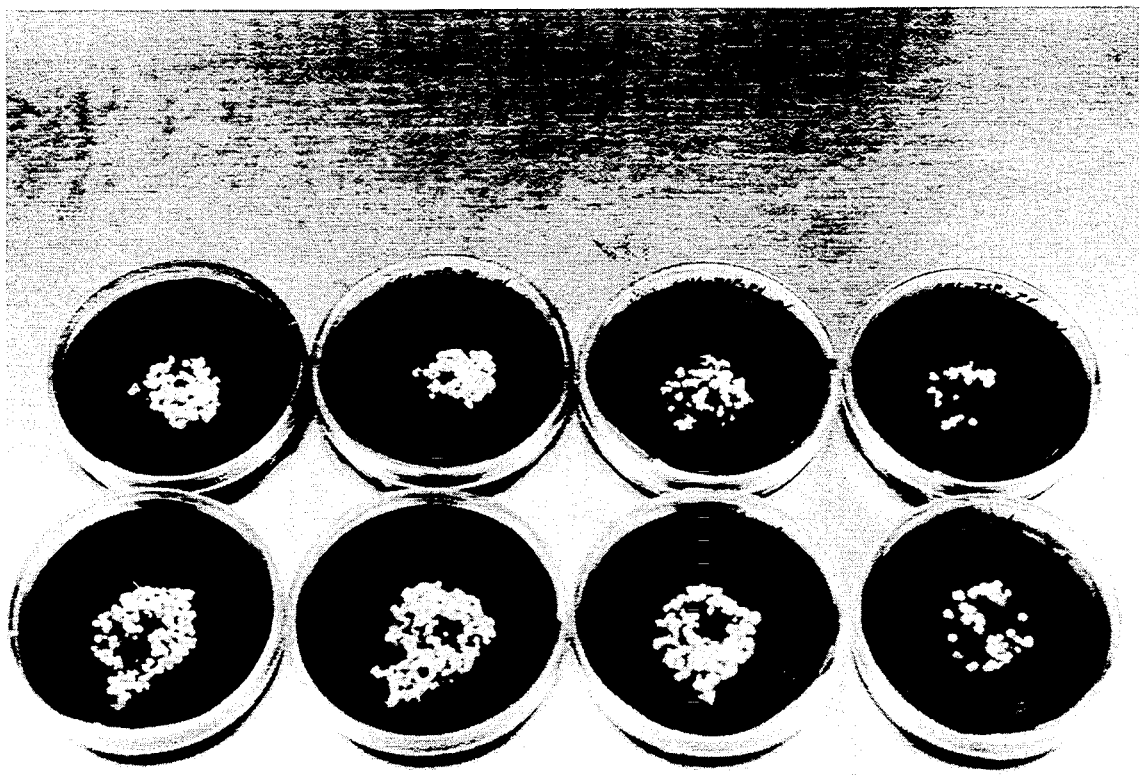

After callus/embryoid formation occurred, embryoids still attached to the nylon raft were transferred to an anther culture medium for embryoid maturation. A full strength, solidified 6N1 medium was used. FIG. 9A and FIG. 9B shows embryogenic tissue on this maturation medium (see Example 6). The dark background results from the activated charcoal.

Figure 10A:
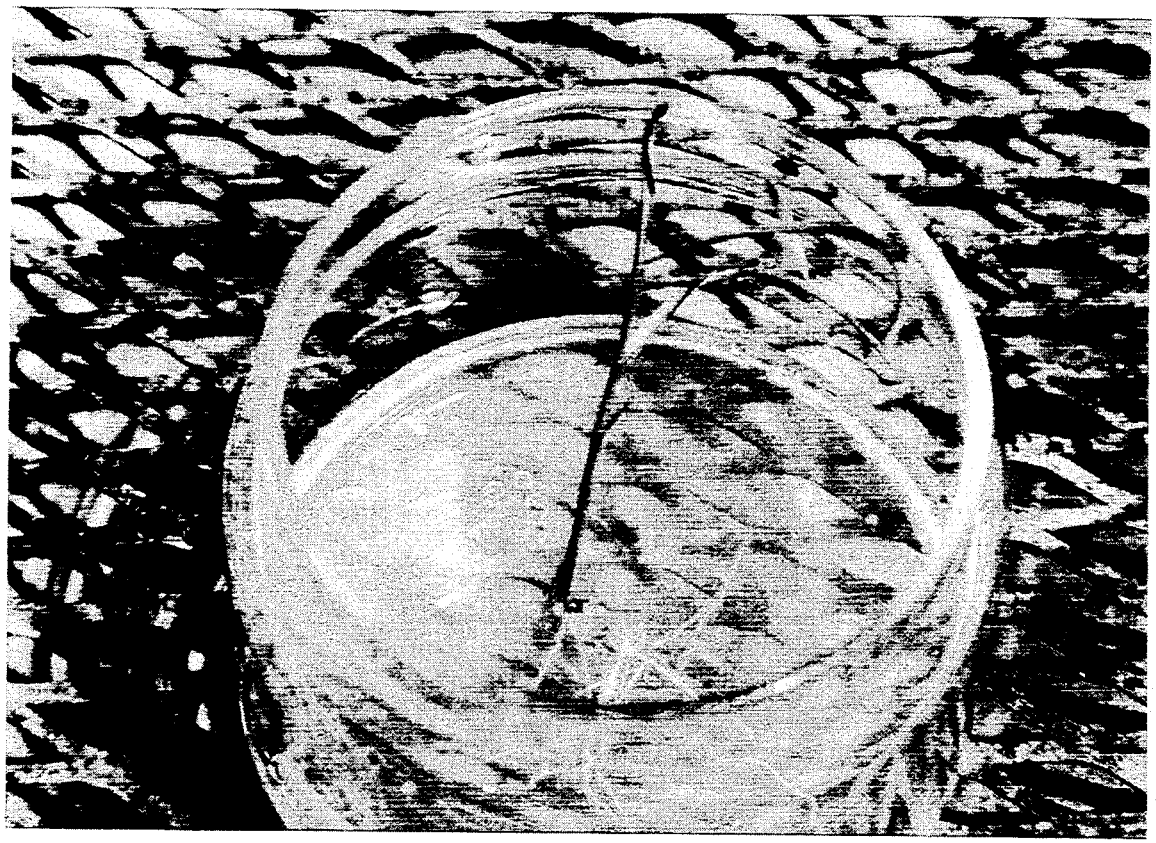
FIG. 10A and FIG. 10B: Regenerated plantlets in the germination phase are shown. Roots and shoots are visible.
Figure 10B:
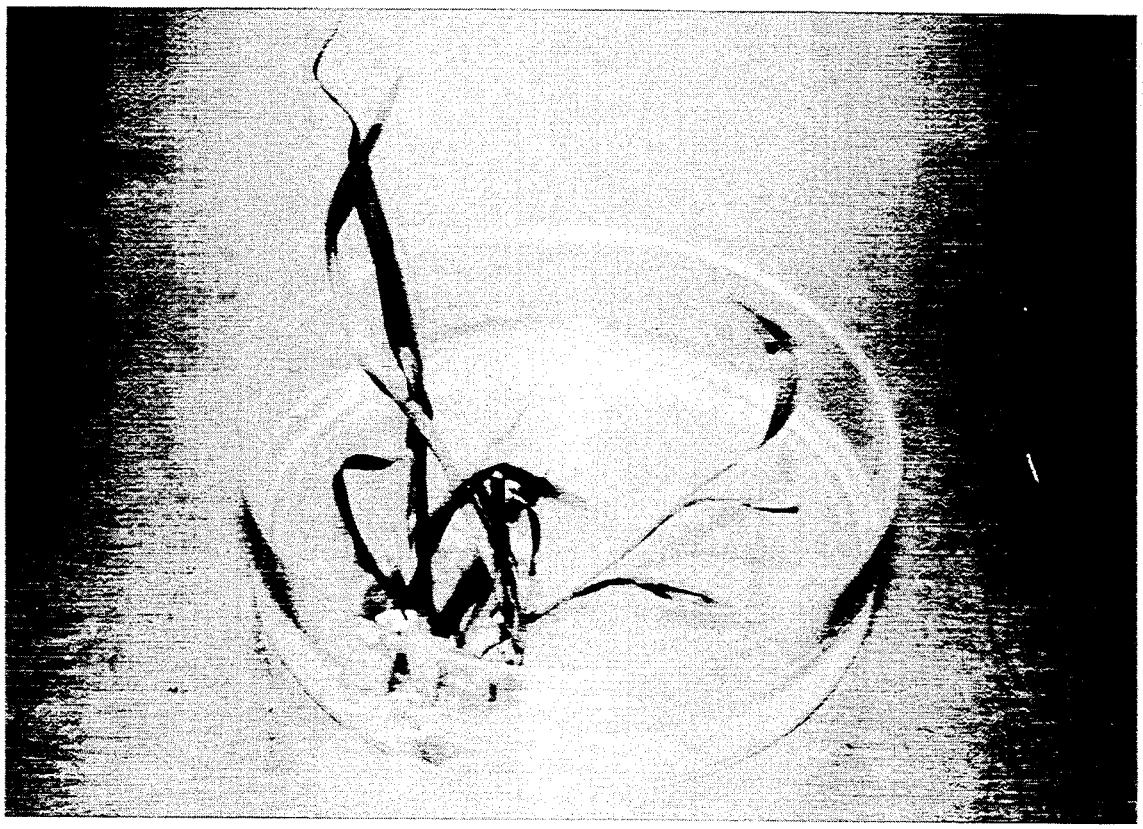

The embryoids developed into plantlets. In the regeneration steps shoot and root initiation occurs (Example 6), as shown in FIG. 10A and FIG. 10B.

Figure 11:
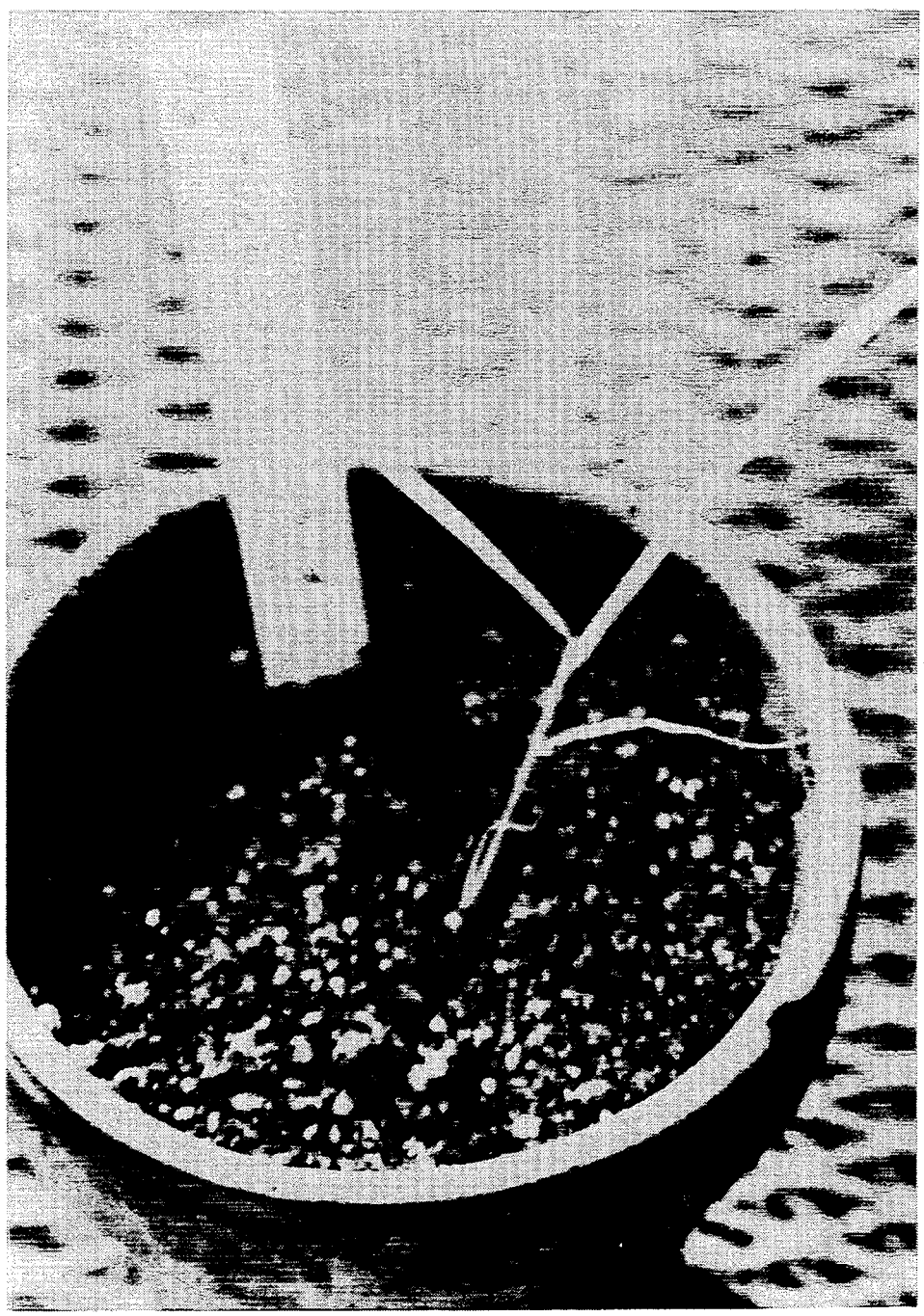
FIG. 11: A newly potted plant which arose from isolated microspore cultures as disclosed herein, is shown.

After the plantlets reached a height of about 5 cm, they were potted as shown in FIG. 11.

Figure 12A:
FIG. 12A and FIG. 12B: A self-pollinated plant which arose from isolated microspore cultures as disclosed herein, is shown.
Figure 12B:
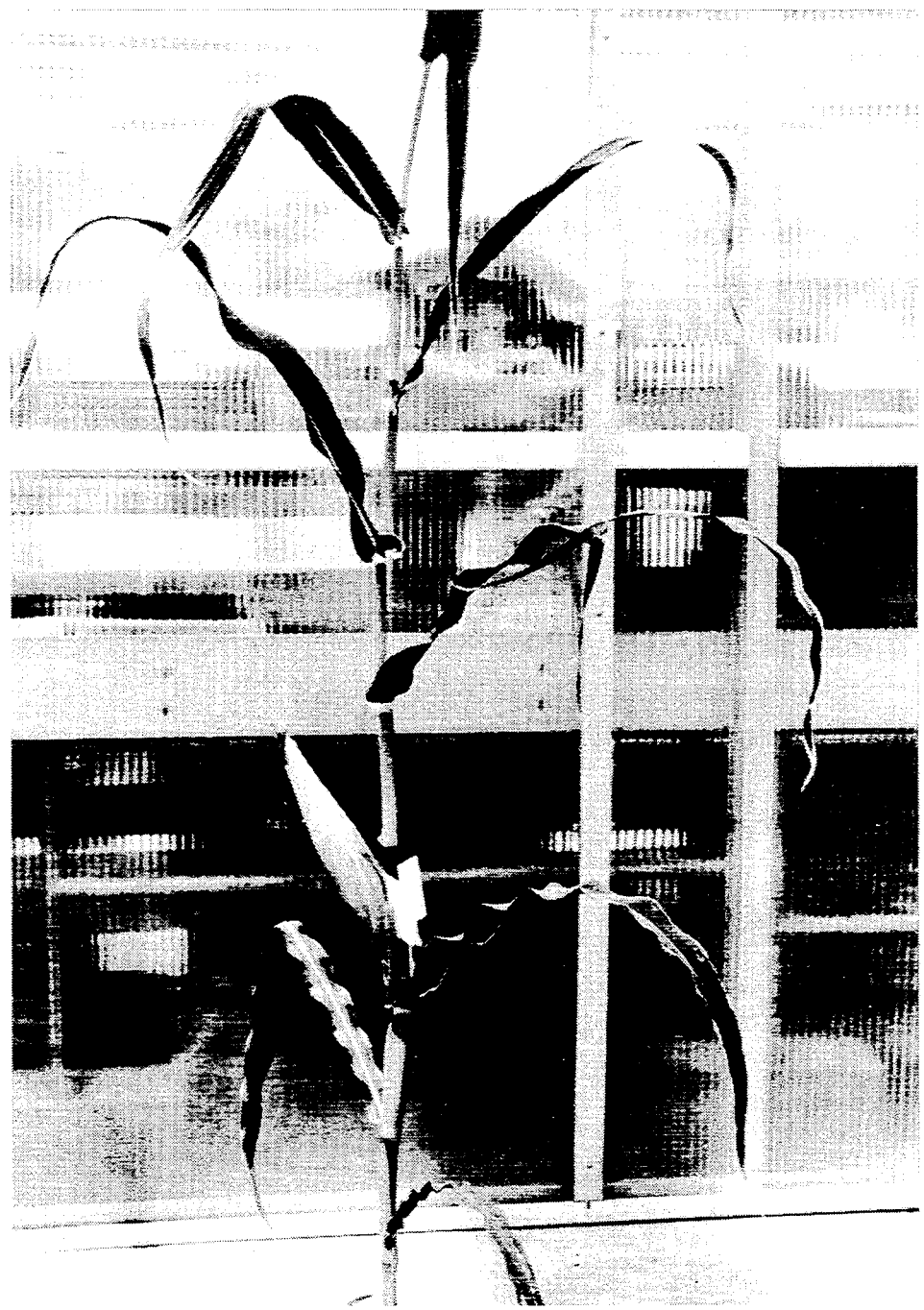

25% of these plants were fertile and produced seeds and progeny. FIG. 12A and FIG. 12B shows a self-pollinated plant that was derived from the isolated microspore cultures disclosed herein.

EXAMPLE 6

Sequence of Media Used to Regenerate Plants from Anther and Isolated Microspore Cultures A sequence of media was used to produce fertile plants from isolated microspore cultures. The same sequences without the isolation and "D" medium were used for anther cultures.

| MEDIA SEQUENCE* |
|---|
| 1. PRECULTURE MEDIUM: (MANNITOL FLOAT) |
| 0.3M MANNITOL + 50 mg/l |
| ASCORBIC ACID + 0.50 mg/l AgNO₃ + 1 mg/l |
| THIAMINE (B₁) + 5 mg/l NICOTINIC ACID + |
| 0.1 mg/l BIOTIN + 0.01% to 0.05% COLCHICINE. |
| 2. ISOLATION MEDIUM: |
| 6% SUCROSE + 50 mg/l ASCORBIC ACID + |
| 400 mg/l PROLINE + 0.1 mg/l BIOTIN + |
| 5 mg/l NICOTINIC ACID. |
| 3. EMBRYOID/CALLUS INDUCING MEDIUM: |
| IMC CULTURE MEDIUM "D": |

-continued

| MEDIA SEQUENCE* |
|---|
| 6N1 (¼X) 0.5 mg/l AgNO₃ |
| 4. EMBRYOID MATURATION MEDIUM: (ANTHER CULTURE MEDIUM) 6N1-TPG-4P or 5002 |
| 5. REGENERATION MEDIUM: |
|   A. SHOOT INITIATION MEDIUM: |
|     CMP¼ + ¼ or 1511 |
|   B. ROOT INITIATION MEDIUM: |
|     3N¼ or 1505 |
|   C. FINISH MEDIUM: |
|     3S6PICAN or 1519 |

*Identifiers used for some medium are code numbers used by the inventors. The detailed composition of these media are in the following sections.

COMPOSITION OF MEDIA

Media 1, 2, 3 above are filter sterilized by methods well known to those skilled in the art. Media 4 and 5 are autoclaved.

| 1. PRECULTURE MEDIUM: (MANNITOL FLOAT) Code: 4002 MAVAC | |
|---|---|
| STOCK | AMOUNT/L |
| Mannitol | 54.7 g (0.3M) |
| Ascorbic Acid | 50 mg |
| AgNO₃ | 0.5 mg |
| KOH | pH 5.7–5.8 |
| Thiamin (B1) | 1 mg |
| Nicotinic Acid | 5 mg |
| Biotin | 0.1 mg |
| Colchicine | 0.1–0.5 g |

| 2. ISOLATION MEDIUM Code: 4501 06AP.1BN | |
|---|---|
| STOCK | AMOUNT/L |
| Sucrose | 60 g |
| Ascorbic Acid | 50 mg |
| Proline | 400 mg |
| Biotin | 0.1 mg |
| Nicotinic Acid | 10 mg |
| KOH | pH 5.7–5.8 |

| 3. EMBRYOID/CALLUS INDUCING MEDIUM: (IMC CULTURE MEDIUM "D") Code: 5500 6N1(¼X) D.5 Ag | | |
|---|---|---|
| STOCK | STOCK SOLUTION | AMOUNT/L |
| 6N1(¼X) D Major | (See below) | 10 ml |
| 6N1 Minor (N6 Minor) | (See below) | 4 ml |
| CaCl₂—2H₂O | (44 mg/ml) | 0.471 |
| FeEDTA | (See below) | 1.25 m |
| Thiamine HCl | (1 mg/ml) | 0.1 ml |
| Nicotinic Acid | (1 mg/ml) | 0.5 mg |
| AgNO₃ | (17 mg/ml) | 0.0294 ml |
| Proline | | 400 mg |
| Casamino Acids | | 30 mg |
| Sucrose | | 120 g |
| KOH | | pH 5.7–5.8 |

This is the standard culture medium for isolated microspores, wherein:

| | | |
|---|---|---|
| Major | KNO₃ | 300 mg |
| | KH₂PO₄ | 50 mg |
| | MgSO₄ (Anhydrous) | 11.43 mg |
| Minor | KI | 0.8 mg |
| | H₃BO₃ | 1.6 mg |
| | MnSO₄—H₂O | 3.33 mg |
| | ZnSO₄—7H₂O | 1.5 mg |
| FeEDTA | CaCl₂—2H₂O | 20.72 mg |
| | Na₂EDTA | 4.66 mg |
| | FeSO₄—7H₂O | 3.475 mg |
| | Thiamine HCl | 0.1 mg |
| | Nicotinic Acid | 0.5 mg |
| | AgNO₃ | 0.5 mg |

4. EMBRYOID MATURATION MEDIUM

-continued

(ANTHER CULTURE MEDIUM)
Code: 5002
6N1-TGR-P4

| STOCK | STOCK SOLUTION | AMOUNT/L |
|---|---|---|
| 6N1 Major | (See below) | 10 ml |
| 6N1 Minor | (See below) | 4 ml |
| CaCl₂—2H₂O | (44 mg/ml) | 3.77 ml |
| FeEDTA | (See below) | 10 ml |
| Thiamine HCl | (1 mg/ml) | 0.1 ml |
| Nicotinic Acid | (1 mg/ml) | 0.5 mg |
| Triiodobenzoic Acid | (1 mg/ml) | 0.1 ml |
| Abscisic Acid | (0.05 mg/ml) | 1 ml |
| Proline | | 400 mg |
| Sucrose | | 120 g |
| KOH | | pH 5.7–5.8 |
| Neutralized Activated Charcoal | | 5 g |
| Gelrite | | 2 g |

Phytagel is an acceptable substitute for Gelrite. There is an enhanced anther response if media contain activated charcoal. This ingredient may absorb toxic or inhibitory substances. The following further define the media:

| Major | KNO₃ | 2.022 g |
|---|---|---|
| | NH₄H₂PO₄ | 384 mg |
| | MgSO₄ (Anhydrous) | 90.4 mg |
| Minor | KI | 0.8 mg |
| | H₃BO₃ | 1.6 mg |
| | MnSO₄—H₂O | 3.33 mg |
| | ZnSO₄—7H₂O | 1.5 mg |
| FeEDTA | CaCl₂—2H₂O | 165.88 mg |
| | Na₂EDTA | 37.3 mg |
| | FeSO₄—7H₂O | 27.8 mc |
| | Thiamine HCl | 1 mg |
| | Nicotinic Acid | 0.5 mg |
| | Triiodobenzoic Acid | 0.1 mg |
| | Abscisic Acid | 0.05 mg |

5. REGENERATION MEDIUM
A. SHOOT INITIATION MEDIUM
Code: 1511
CMP¼ + ¼

| STOCK | STOCK SOLUTION | AMOUNT/L |
|---|---|---|
| MS Major | (See below) | 10 ml |
| Ms Minor | (See below) | 1 ml |
| CaCl₂—2H₂O | (44 mg/mi) | 10 ml |
| FeEDTA | (See below) | 10 ml |
| Thiamine HCl | (See below) | 0.5 ml |
| Niacin | (See below) | 0.5 ml |
| Coconut Milk | | 20.4 ml |
| Sucrose | | 30 mg |
| Proline | | 100 mg |
| BAP | (0.1 mg/1 ml) | 2.5 ml |
| Abscisic Acid | (0.05 mg/1 ml) | 1 ml |
| NAA | (0.1 mg/ml) | 2.5 ml |
| MES | | 195 mg |
| Gelrite | | 1.8 g |
| KOH | | pH 5.7–5.8 |

This medium has been used for a variety of somaclone tissue culture and anther culture genotypes. It is used as an initial stepdown. The proline and coconut milk enhance this media as compared to 3N¼+¼ or 1520. The medium causes development of shoot tissue.

THESE ARE THE SAME FOR ALL MS MEDIA

| Major | NH₄NO₃ | 1.65 g |
|---|---|---|
| | KNO₃ | 1.90 g |
| | KH₂PO₄ | 170 mg |
| | MgSO₄ (Anhydrous) | 181 mg |
| Minor | KI | 0.832 mg |
| | H₃BO₃ | 6.2 mg |
| | MnSO₄—H₂O | 16.92 mg |
| | ZnSO₄—7H₂O | 8.6 mg |
| | Na₂MO₄—2H₂O | 0.252 mg |
| | CUSO₄—5H₂O | 0.0252 mg |
| | COCl₂—6H₂O | 0.0252 mg |
| FeEDTA | CaCl₂—2H₂O | 440 mg |
| | Na₂EDTA | 37.3 mg |
| | FeSO₄—7H₂O | 27.8 mg |
| | Thiamine HCl | 0.5 mg |
| | Niacin | 0.5 mg |
| | BAP | 0.25 mg |
| | Abscisic Acid | 0.05 mg |
| | NAA | 0.25 mg |

B. ROOT INITIATION
Code: 1505
3N¼

| STOCK | STOCK SOLUTION | AMOUNT/L |
|---|---|---|
| MS Major | (See 1511) | 10 ml |
| MS Minor | (See 1511) | 1 ml |
| CaCl₂ | (44 mg/ml) | 10 ml |
| FeEDTA | (See 1511) | 10 ml |
| Thiamine HCl | (1 mg/ml) | 0.5 mg |
| Niacin | (1 mg/ml) | 0.5 mg |
| Sucrose | | 30 mg |
| ABA | (0.05 mg/1 ml) | 0.05 mg |
| NAA | (0.1 mg/ml) | 0.25 mg |
| MES | | 195 mg |
| Gelrite | | 1.8 g |
| KOH | | pH 5.7–5.8 |

This medium is used between shoot initiation and final rooting or can be used as a final rooting medium. After tissue begins to develop shoots it can be moved to 1505 to enhance root development. Shoot elongation and roots develop. Some genotypes of somaclonal tissue culture and anther culture develop into mature plantlets and can go directly to soil, while root develop isn't complete for others. In this case, the plantlet is moved to a rooting medium such as 1519 (next section).

C. "FINISHING" MEDIUM
Code: 1519
3S6PICAN

| STOCK | STOCK SOLUTION | AMOUNT/L |
|---|---|---|
| Ms Major | (See 1511) | 10 ml |
| MS Minor | (See 1511) | 1 ml |
| CaCl₂ | (44 mg/ml) | 10 ml |
| FeEDTA | (See 1511) | 10 ml |
| Thiamine HCl | (1 mg/ml) | 0.5 mg |
| Niacin | (1 mg/ml) | 0.5 mg |
| Sucrose | | 30 mg |
| Proline | | 600 mg |
| Casamino Acid | | 100 mg |
| Abscisic Acid | (0.05 mg/1 ml) | 0.05 mg |
| NAA | (0.1 mg/ml) | 0.1 mg |
| MES | | 195 mg |
| Agar (Phytagar) | | 7 g |
| KOH | | pH 5.7–5.8 |

Medium 1519 is used as a rooting or finishing medium. The addition of casamino acids and NAA give certain plants a boost not seen when using 3S6P only.

| STOCK | COMPOUND | AMOUNT | TOTAL VOLUME | CONCENTRATION |
|---|---|---|---|---|
| MAJOR STOCK FORMULATIONS | | | | |
| MS Major | $NH_4NO_3$ | 165.0 g | 1000 ml | 100X |
| | $KNO_3$ | 190.0 g | | |
| | $KH_2PO_4$ | 17.0 g | | |
| | $MgSO_4$ (Anhydrous) | 18.1 g | | |
| 6N1 Major | $KNO_3$ | 202.2 g | 1000 ml | 100X |
| | $NH_4H_2PO_4$ | 38.4 g | | |
| | $MgSO_4$ (Anhydrous) | 9.04 g | | |
| 6N1 (⅙X) D Major | $KNO_3$ | 30 g | 1000 ml | 100X |
| | $KH_2PO_4$ | 5 g | | |
| | $MgSO_4$ (Anhydrous) | 1.143 g | | |
| MINOR STOCK FORMULATIONS | | | | |
| MS Minor | KI | 0.208 g | 250 ml | 1000X |
| | $H_3BO_3$ | 1.550 g | | |
| | $MnSO_4.H_2O$ | 4.230 g | | |
| | $ZnSO_4.7H_2O$ | 2.150 g | | |
| | $Na_2MoO_4.2H_2O$ | 0.063 g | | |
| | $CuSO_4.5H_2O$ | 0.0063 g | | |
| | $COCl_2.6H_2O$ | 0.0063 g | | |
| 6N1 (N6) Minor | KI | 0.200 g | 1000 ml | 250X |
| | $H_3BO_3$ | 0.400 g | | |
| | $MnSO_4.H_2O$ | 0.833 g | | |
| | $ZnSO_4.7H_2O$ | 0.375 g | | |
| OTHER STOCK FORMULATIONS | | | | |
| FE.EDTA (MS, N6, B5 and SH) | $Na_2EDTA$ | 3.730 g | 1000 ml | 100X |
| | $FeSO_4.7H_2$ | 2.780 g | | |

Special Instructions: dissolve $NA_2EDTA$ first, then $FeSO_4.7H_2O$.
Autoclave 2 minutes.

EXAMPLE 7

Effect of a Combination of Stresses on Response to Anther Cultures

Fresh anthers without cold pretreatment were floated on 0.3 M mannitol for 4 days at 28° C. Mannitol proved to be as effective as a cold pretreatment of the tassel for 14 days at 10° C. When the 2 treatments were combined a dramatic increase in response rate was observed.

TABLE III

The Effect of Mannitol Preculture Medium and Cold Incubation on Anther Response[a,b]

| Cold Pre-treatment | Preculture of Anthers | # of Plates | Microspore Density | Total Responses (Per $10^4$) |
|---|---|---|---|---|
| None | 4 days at 28° C. on 0.3M Mannitol | 3 | $7.3 \times 10^4$ | 25(1.14) |
| None | 4 days at 28° C. on 0.3M Mannitol plus 50 mg/l Ascorbic Acid | 3 | $7.0 \times 10^4$ | 55(2.62) |
| 16 days at 10° C. | None | 1 | $7.8 \times 10^4$ | 12(1.54) |
| None | 14 days at 10° C. 0.3M Mannitol + 50 mg/l Ascorbic Acid | 2 | $7.14 \times 10^4$ | 169(11.83) |

[a]Isolation Medium - 6% sucrose + 50 mg/l Ascorbic acid + 400 mg/l Proline + 0.1 mg/l Biotin + 5 mg/l Nicotinic Acid
[b]Culture Medium - Bilayer Plates

EXAMPLE 8

Comparison of Supports for Microspores During Culture

Tassels were pretreated for 8 days at 10° C. Dissected anthers were incubated at 10° C. for 17 days with a preculture medium comprising 0.3 M Mannitol and 50 mg/l ascorbic acid. The isolation medium was 6% sucrose +50 mg/l Ascorbic Acid +400 mg/l Proline +0.1 mg/l Biotin +5 mg/l Nicotinic Acid. The nylon raft culture system was superior to either the Transwell plates or the bilayer plates.

TABLE IV

Transwell Plates vs. Nylon Rafts vs. Bilayer Plates

| # of Plates | Support and Culture Medium | Microspore Density | Responses | Responses Per $10^4$ Microspores |
|---|---|---|---|---|
| 1 | D in Transwell | $6.8 \times 10^4$ | 155 | 22.79 |
| 1 | D with nylon raft | $6.8 \times 10^4$ | 171 | 25.15 |
| 2 | D Bilayer | $6.8 \times 10^4$ | 159 | 11.69 |

EXAMPLE 9

Colchicine Treatment of Whole Anthers During Preculture and the Improved Response Rate of the Isolated Microspore Cultures The preculture medium (4002) was supplemented with 0.01, 0.025, and 0.05% colchicine and compared to an unsupplemented control. Given the reported toxicity of colchicine on isolated microspores, it was surprising that all levels of colchicine tested were superior to the control. The preferred concentration is 0.01%. The isolation medium was 6% sucrose+50 mg Ascorbic Acid+400 mg/l Proline+0.1 mg/l Biotin+10 mg/l Nicotinic Acid (designated 4501, Example 6). After a 2 week incubation period on D medium, nylon rafts with embryoids were serially transferred to 6N1-TGR-P4, a solidified anther culture medium (see Example 6).

TABLE V

Effect of Colchicine on Responses for Isolated Microspore Cultures

| Cold Pretreatment and Preculture | # of Plates | Microspore Density | Re-sponses | Responses Per $10^4$ Microspores |
|---|---|---|---|---|
| 4 days at 10° C. (Tassels) then 10 days at 10° C. in 0.3M Mannitol + 50 mg/l Ascorbic Acid + 0.5 mg/l AgNO$_3$ + 1 mg/l B$_1$ + 5 mg/l Nicotinic Acid + 0.1 mg/l Biotin (designated MAVA) | 5 | $8.5 \times 10^4$ | 1252 | 29.12 |
| MAVA + 0.01% Colchicine | 3 | $8.4 \times 10^4$ | 1892 | 75.08 |
| MAVA + 0.025% Colchicine | 3 | $8.8 \times 10^4$ | 1136 | 43.03 |
| MAVA + 0.05% Colchicine | 5 | $8.0 \times 10^4$ | 2040 | 51.00 |

The following media descriptions relate to studies reported hereinbelow in Examples 10–13.

I. Preculture Media
4000 0.3M Mannitol + 50 mg/L Ascorbic Acid
4019 0.3M Mannitol + 50 mg/L Ascorbic Acid + 0.025% Colchicine
4022 4019 + 3.3 mg/L Dicamba
4030 0.3M Mannitol + 50 mg/L Ascorbic Acid + 5 μM ARM
4034 0.3M Mannitol + 75 mg/L Ascorbic Acid + 0.025% Colchicine
4035 0.3M Mannitol + 100 mg/L Ascorbic Acid + 0.025% Colchicine
4036 0.3M Mannitol + 150 mg/L Ascorbic Acid + 0.025% Colchicine II. Isolation Media
4502 06AP.1B1ON-6% Sucrose + 400 mg/L Proline + 50 mg/L Ascorbic Acid + 0.1 mg/L Biotin + 10 mg/L Nicotinic Acid
4504 6% Maltose + 400 mg/L Proline + 50 mg/L Ascorbic Acid + 0.1 mg/L Biotin + 10 mg/L Nicotinic Acid III. Anther Culture Media
5002 6N1-TPG-P4 - Standard Anther Culture Medium with 12% Sucrose
5018 Anther Culture Medium with 12% Maltose replacing Sucrose IV. Microspore Culture Media
5500 6N1 (½x)D.5Ag or "D"
5536 5500 with 12% Maltose replacing Sucrose
5539 5500 with 6% Sucrose and 6% Maltose

EXAMPLE 10

Effects of a Reduced Temperature on Microspore Isolation

Tassels were obtained from corn plants of line G238 (6743×FBJW) and precultured at 10° C. for 10 days. Anthers were dissected out of the tassels, placed in about 3 ml of preculture medium designated 4019 and incubated at a temperature of about 10° C. for 22 days.

Microspores were isolated from anthers by chopping the anthers into pieces with a razor blade. The resulting mixture of released microspores, anther fragments and isolation medium was then passed through a nylon mesh filter to separate the microspores from the anther wall fragments. The filtrate was then washed several times in isolation medium.

Microspores were isolated either at room temperature or under chilled conditions where the isolation medium, razor blades, funnels, centrifuge tubes and centrifuge tube holders were refrigerated prior to use. In addition, the Petri dish containing the anthers was placed over ice during the chopping process. The "chilled" method kept the microspores cold from the time of anther chopping until at least the end of the first washing.

Embryoid/calli formation was induced by culturing the isolated microspores for 14 days in culture medium designated 5500, then in culture medium designated 5002. The formation of embryoids was determined and the results of these studies are summarized in Table VI.

The response rate was higher by 70% using the "chilled" method with 5.78 embryoids per 104 microspores versus 3.38 embryoids per $10_4$ microspores for the room temperature method.

EXAMPLE 11

The Effects of Ascorbic Acid

Tassels were obtained from corn plants as set forth in Example 10 and incubated at about 10° C. for 5 days. Anthers were dissected out of the tassels and separated into four aliquots. Individual aliquots were placed in about 3 ml of four different preculture medium designated 4019, 4034, 4035 and 4036, respectively and incubated at a temperature of about 10° C. for 22 days. The concentration of ascorbic acid in those preculture media was 50 mg/l, 75 mg/l, 100 mg/l and 150 mg/l, respectively.

Microspores were isolated under chilled conditions and cultured in induction media as set forth in Example 10. The results of these studies are summarized in Table VI. The level of embryoid production was greatly increased when 75 mg/L or 100 mg/L ascorbic acid was used with 75 mg/L being the best level. 150 mg/L ascorbic acid in the preculture medium was detrimental where compared to 50 mg/l.

EXAMPLE 12

Effects of Maltose

Tassels were obtained from corn plants as set forth in Example 10 and incubated at about 10° C. for 2–7 days. In one study (Example 12a), anthers were dissected out of the tassels after 3 days, placed in about 3 ml of preculture medium designated 4019 and incubated at a temperature of about 10° C. for 21 days.

Microspores were isolated under chilled conditions as set forth in Example 10, placed on nylon rafts and cultured in induction media designated 5500 for 14 days. The microspore cultures were then separated into two aliquots. One aliquot was transferred to induction medium designated 5002 and the other aliquot transferred to induction medium designated 5018. Medium 5002, a solid medium, contained 12% sucrose. Medium 5018, a solid medium, contained 12% maltose. Embryoid formation was determined and the results of this study are summarized in Table VI. The response rate using maltose (5018) was 31% better than sucrose.

In a second study (Example 12a), after 2 days of tassel preculture, anthers were precultured in preculture medium designated 4000 at 10° C. for 15 days. Microspores were isolated under chilled conditions as set forth in Example 10, separated into two aliquots and the aliquots placed on nylon rafts. One aliquot was cultured in induction media designated 5500 for 15 days and then transferred to induction medium designated 5002. The other aliquot was cultured in induction medium designated 5536 for 15 days and then transferred to induction medium designated 5018. Medium 5500 and medium 5002 comprise 12% sucrose. Medium 5536 and medium 5018 comprise 12% maltose.

The results of these studies (12b) are summarized in Table VI. Microspores cultured on sucrose had a response rate of 1.97 embryoids per $10_4$ microspores while the maltose cultured microspores had a response rate of 89.6 embryoids per 104 microspores. These data indicate that maltose can greatly improve the induction rate of microspores even when the donor material has very poor vigor as seen with the control, sucrosetreated microspores.

In a third study (Example 12c), after 7 days of tassel preculture, anthers were precultured in preculture medium designated 4030 for 15 days at about 10° C. Microspores were isolated under chilled conditions in isolation medium designated 4504, which medium comprised 6% maltose instead of the standard 6% sucrose (preculture medium designated 4502).

Isolated microspores were separated into three aliquots and placed on nylon rafts. One aliquot was cultured in induction medium designated 5500 for 14 days. A second aliquot was cultured in induction medium designated 5539 for 14 days. A third aliquot was cultured in induction medium designated 5536 for 14 days. Medium 5500 comprised 12% sucrose. Medium 5539 comprised 6% sucrose +6% maltose. Medium 5536 comprised 12% maltose.

Embryoid formation was determined and the results of these studies are summarized in Table VI. The data show that the response rate seen on the mixture of maltose and sucrose was 50% higher than on the pure sucrose medium. The response rate from the pure maltose medium was more than 3½ times that seen on the pure sucrose medium. The induction rate of 115.70 embryoids per $10_4$ microspores seen in cultures of pure maltose indicate that exposure to maltose early in the culturing process is likely very important to obtaining high response rates.

EXAMPLE 13

Effects of a Growth Regulator in a Preculture Medium

Tassels were obtained from corn plants as set forth in Example 10 and incubated at about 10° C. for 1 day. Anthers were dissected out of the tassels and separated into two aliquots. One aliquot was placed in a preculture medium designated 4019 and incubated at a temperature of about 10° C. for 14 days. The other aliquot was placed in a preculture medium designated 4022 and incubated at a temperature of about 10° C. for 14 days. Medium 4022 contains the growth regulator dicamba. Medium 4019 does not contain any growth regulators.

Microspores were isolated under chilled conditions as set forth in Example 10, placed on nylon rafts and cultured in induction media designated 5500 for 14 days. The microspore cultures were then transferred to induction medium designated 5002.

The results of these studies are summarized in Table VI. The data show that the dicamba preculture medium gave a 53% greater response rate over the control with no growth regulators.

TABLE VI

| Example | Cold Pre-Trt/ Precultures | Isolation Medium | Culture Medium | M'spore Density | # of Rspns | Respns per $10^4$ Mic |
|---|---|---|---|---|---|---|
| 10 | 7d10° Tassel 22d10° 4019 | 4502 Isolated at rm. temp. | 5500 (14d), then 5002 | $7.77 \times 10^4$ | 184 | 3.38 |
|  |  | 4502 Isolated under chilled conditions | 5500 (14d), 5002 | $7.63 \times 10^4$ | 353 | 5.78 |
| 11 | 5d10° Tassel 21d10° 4019 | 4502 | 5500 (14d), 5002 | $7.3 \times 10^4$ | 697 | 13.64 |
|  | 5d10° Tassel 21d10° 4034 | 4502 | 5500 (14d), 5002 | $6.8 \times 10^4$ | 2335 | 42.92 |
|  | 5d10° Tassel 21d10° 4035 | 4502 | 5500 (14d), 5002 | $6.9 \times 10^4$ | 1605 | 33.23 |
|  | 5d10° Tassel 21d10° 4036 | 4502 | 5500 (14d), 5002 | $7.5 \times 10^4$ | 555 | 10.57 |
| 12a | 3d10° Tassel 21d10° 4019 | 4502 | 5500 (14d), 5002 | $7.4 \times 10^4$ | 130 | 4.39 |
|  |  |  | 5500 (14d), 5018 | $7.4 \times 10^4$ | 128 | 5.77 |
| 12b | 2d10° Tassel | 4502 | 5500 (15d), 5002 | $7.63 \times 10^4$ | 60 | 1.97 |

TABLE VI-continued

| Example | Cold Pre-Trt/ Precultures | Isolation Medium | Culture Medium | M'spore Density | # of Rspns | Respns per $10^4$Mic |
|---|---|---|---|---|---|---|
| | 15d10° 4000 | | 5536 (15d), 5018 | $7.63 \times 10^4$ | 1368 | 89.6 |
| 13 | 1d10° Tassel 14d10° 4019 | 4502 | 5500 (14d), 5002 | $7.7 \times 10^4$ | 151 | 9.81 |
| | 1d10° Tassel 14d10° 4022 | 4502 | 5500 (14d), 5002 | $7.3 \times 10^4$ | 219 | 15.0 |
| 12c | 7d10° Tassel | 4504 | 5500 (14d), 5002 | $8.28 \times 10^4$ | 774 | 31.16 |
| | 15d10° 4030 | | 5539 (14d), 5002 | $8.28 \times 10^4$ | 1559 | 47.07 |
| | | | 5536 (14d), 5002 | $8.28 \times 10^4$ | 3832 | 115.70 |

While the invention is susceptible to various modifications and alternative forms, specific embodiments thereof have been shown by way of example in the drawings and herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

REFERENCES

The references listed below are incorporated herein by reference to the extent that they supplement, explain, provide a background for, or teach methodology, techniques, and/or compositions employed herein.

Reference 1. Anonymous, 401 Research Group (1975) Primary study on induction of pollen plants of Zea mays (English abstract). Acta Genet. Sin. 2:143.

Reference 2. Brettell, R.I.S., Thomas E., Wernicke W. (1981) Production of haploid maize plants by anther culture. Maydica 26:101–111.

Reference 3. Chu, C. C. (1981) The N6 medium and its applications to anther culture of cereal crops. Proc. Symp. Plant tissue culture, Beijing 1978. Pitman, Boston, pp. 43–50.

Reference 4. Close, K. R., Ludeman, L. A. (1987) The effect of auxin-like plant growth regulators and osmotic regulation on induction of somatic embryogenesis from elite maize inbreds. Plant Sci. 52:81–89.

Reference 5. Coumans, M. P., Sohota, S. and Swanson, E. B., (1989) Plant development from isolated microspores of Zea mays L. Plant Cell Reports 7:618–621.

Reference 6. Dieu, P., Becker, M. (1986) Further studies of androgenetic embryo production and plant regeneration from in vitro cultured anthers in maize (Zea mays) L. Maydica 31:245–259.

Reference 7. Duncan, D. R., Williams, M. E., Zehr, B. E., Widholm, J. M. (1985) The production of callus capable of plant regeneration from immature embryos of numerous Zea mays genotypes. Planta 165:322–332.

Reference 8. Foroughi-Wehr, B., Mix G., Gaul H., Wilson, H. M. (1976) Plant production from cultured anthers of Hardeum vulgare LIZ Pflangenzuecht 77:198–204.

Reference 9. Genovesi, A. D., Collins, G. B. (1982) In vitro production of haploid plants of corn via anther culture. Crop Sci 22:1137–1144.

Reference 10. Hunter, C. P. (1987) Plant generation method. European Patent Appln. 0245898A2 Bulletin 87/47.

Reference 11. Jensen, C. J. (1974) Chromosome doubling techniques in haploids. In: Kasha K. J. (ed) Haploids in higher plants: advances and potentials. Univ. Press, Goelph, pp. 153–190.

Reference 12. Keller, W. A., Annison, P. G., Cardy, B. J. (1987) Haploids from gametophytic cells recent development and future prospects. Plant Tissue and Cell Culture, Alan R. Liss., Inc. pp. 223–241.

Reference 13. Ku, M. K., Cheng, W. C., Kuo, L. C., Kuan, Y. L., An, H. P. Huang, C. H. (1981) Induction factors and morphocytological characteristics of pollen-derived plants in maize (Zea mays). Proc. Symp plant tissue culture. Beijing 1978. Pitman, Boston, pp. 35–42.

Reference 14. Kuo, C. S., Lu, W. L., Kui, Y. L. (1985) Corn (Zea mays L.); Production of pure lines through anther culture. In: Bajaj, YPS (ed) Biotechnology in Agriculture and Forestry, Vol. 2. Crops I. Springer N.Y. pp. 152–164.

Reference 15. Miao, S. H. (1980) Effect of different ammonium salts on the formation of maize pollen embryoids. Acta Bot Sin 22:356–359.

Reference 16. Miao, S. H., Kuo, C. S., Kwei, Y. L., Sun, A. T., Ku, S. Y., Lu, W. L., Wang, Y. Y. (1981) Induction of pollen plants of maize and observations on their progeny. Proc. Symp. Plant tissue culture, Beijing 1978. Pitman, Boston, pp. 23–34.

Reference 17. Murashige, T, Skoog, F, (1962) A revised medium for rapid growth and bioassays with tobacco tissue cultures. Physiol Plant 15:473–497.

Reference 18. Nitsch, C., Andersen, S., Godard, M., Neuffer, M. G., Sheridan, W. F., (1987) Production of haploid plants of Zea mays and Pennisetum through androgenesis. In: Earle E. D., Demarly Y. (eds) Variability in plants regenerated from tissue culture. Praeger, New York, pp. 69–91.

Reference 19. Olsen, F L (1987) Induction of microspore embryogenesis in cultured anthers of Hardeum vulgare: The effects of ammonium nitrate, glutamine and asparagine as nitrogen sources. Carlsberg Res. Commun. 52:393–404.

Reference 20. Pace, G. M., Reed, J. N., Ho, L. C., Fohey, J. W. (1987) Anther culture of maize and the visualization of embryogenic microspores by fluorescent microscopy. Theor. Appl. Genet. 73:863–869.

Reference 21. Pauk, J. (1985) Production of Haploid plants of maize (*Zea mays* L.) through androgenesis. Cereal Res. Commun. 13:47–53.

Reference 22. Pescitelli, S. M., Mitchell, J. C., Jones, A. M., Pareddy, D. R., and Petolino, J. F. (1989) High frequency androgenesis from isolated microspores of maize. Plant Cell Reports 7:673–676.

Reference 23. Petolino, J. F., Jones, A. M. (1986) Anther culture of elite genotypes of *Zea mays* L. Crop Sci. 26:1027–1074.

Reference 24. Petolino, J. F., Jones, A. M., Thompson, S. A. (1988) Selection for increased anther culture response in maize. Theor. Appl. Genet. 76:157–159.

Reference 25. Petolino, J. F., Thompson, S. A. (1987) Genetic analysis of anther culture response in maize. Theor. Appl. Genet. 74:284–286.

Reference 26. Rhodes, C. A., Lowe, K. S., Ruby, K. L. (1988) Plant regeneration from protoplasts isolated from embryogenetic maize cell cultures. Biotechnology 6:56–60.

Reference 27. Sletten, M. C., Tomes, D. F., (1987) Plant recovery from type I and type II embryogenic callus in maize. In Vitro 23:26A.

Reference 28. Songstad, D. D., Duncan, D. R., and Widholm, J. M. (1988) Effect of 1-aminocyclopropane-1-carboxylic acid, silver nitrate, and norbornadiene on plant regeneration from maize callus cultures. Plant Cell Reports 7:262–265.

Reference 29. Sorvart, S. (1986) The effect of starch gelatinized nutrient media in barley anther cultures. Annales Agriculture Fenniae, 25:127–133.

Reference 30. Sunderland, N (1979) Anther and pollen culture 1974–1979. pp. 171–183 in The Plant Genome and 2nd Int. Haploid Conference. John Innes Symp.

Reference 31. Ting, Y. C., Yu, M., Zheng, W. Z. (1981) Improved anther culture of maize (*Zea mays*). plant Sci. Lett. 23:139–145.

Reference 32. Wan, Y., Petolino, J. F., Widholm, J. M. (1989) Efficient production of haploid plants through colchicine treatment of anther-derived maize callus. Theor. Appl. Genet. 77:889–892.

Reference 33. Wei, Z. M., Kyo, M., and Harada, H. (1986) Callus formation and plant regeneration through direct culture of isolated pollen of *Hordeum vulgare* cv. 'Sabarlis'. Theor. Appl. Genet. 72:252–255.

Reference 34. Gaillard, Vergne, and Beckert [Plant Cell Reports (1991) 10:55–58].

What is claimed is:

1. A method for producing a corn plant, said method comprising the steps of:
    (a) preculturing a corn plant composition that contains microspores at a temperature of from about 8° C. to about 14° C. in a preculture medium comprising a sugar alcohol and colchicine;
    (b) isolating the microspores in an isolating medium to produce isolated, viable microspores;
    (c) placing said microspores on a porous support situated on the surface of an embryoid/callus promoting medium that contains maltose to obtain embryoids or calli; and
    (d) regenerating a plant from the embryoids or calli.

2. The method of claim 1, wherein the plant composition comprises tassels.

3. The method of claim 1, wherein the plant composition comprises anthers.

4. The method of claim 1, wherein the sugar alcohol is mannitol.

5. The method of claim 1, wherein the isolating medium comprises a growth regulator.

6. The method of claim 5, wherein the growth regulator is dicamba.

7. The method of claim 1, wherein the porous support is a mesh raft having a pore size of about 10 microns.

8. The method of claim 1, wherein regenerating comprises sequentially subculturing said embryoids or calli in a series of regeneration media.

9. The method of claim 1, wherein the regenerated plant is fertile.

10. The method of claim 1, further defined as producing seeds and progeny from the regenerated plant.

11. A method for producing a corn plant, said method comprising the steps of:
    (a) preculturing a corn plant composition that contains anthers in a preculture medium under conditions that include a temperature of from 8° C. to about 14° C., a sugar alcohol in the preculture medium, and colchicine in the preculture medium;
    (b) culturing the anthers in a callus/embryoid promoting medium that contains maltose to obtain embryoids or calli; and
    (c) regenerating a plant from the embryoids or calli.

12. The method of claim 1 wherein preculturing lasts from about 7 to about 14 days.

13. The method of claim 11 wherein preculturing lasts from about 7 to about 21 days.

14. The method of claim 11, wherein the regenerated plant is fertile.

* * * * *